United States Patent
Standke et al.

(10) Patent No.: US 9,828,392 B2
(45) Date of Patent: *Nov. 28, 2017

(54) LOW CHLORIDE COMPOSITIONS OF OLEFINICALLY FUNCTIONALISED SILOXANE OLIGOMERS BASED ON ALKOXYSILANES

(71) Applicant: Evonik Degussa GmbH, Essen (DE)

(72) Inventors: Burkhard Standke, Loerrach (DE); Kerstin Weissenbach, Gengenbach (DE); Jaroslaw Monkiewicz, Rheinfelden (DE); Sven Roth, Schwoerstadt (DE); Bernd Nowitzki, Marl (DE)

(73) Assignee: Evonik Degussa GmbH, Essen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/360,120

(22) PCT Filed: Nov. 19, 2012

(86) PCT No.: PCT/EP2012/072964
§ 371 (c)(1),
(2) Date: May 22, 2014

(87) PCT Pub. No.: WO2013/076032
PCT Pub. Date: May 30, 2013

(65) Prior Publication Data
US 2014/0296555 A1  Oct. 2, 2014

(30) Foreign Application Priority Data

Nov. 22, 2011 (DE) .......................... 10 2011 086 865

(51) Int. Cl.
| | | |
|---|---|---|
| C07F 7/18 | (2006.01) | |
| C07F 7/08 | (2006.01) | |
| C09D 183/04 | (2006.01) | |
| C08G 77/20 | (2006.01) | |
| C09J 183/04 | (2006.01) | |
| C08L 83/04 | (2006.01) | |

(52) U.S. Cl.
CPC .......... *C07F 7/0874* (2013.01); *C07F 7/0849* (2013.01); *C08G 77/20* (2013.01); *C08L 83/04* (2013.01); *C09D 183/04* (2013.01); *C09J 183/04* (2013.01)

(58) Field of Classification Search
USPC ......................................... 556/450, 457, 458
See application file for complete search history.

(56) References Cited

U.S. PATENT DOCUMENTS

| | | | |
|---|---|---|---|
| 4,563,261 A | 1/1986 | Staab et al. | |
| 5,282,998 A | 2/1994 | Horn et al. | |
| 5,885,341 A | 3/1999 | Standke et al. | |
| 6,395,856 B1 | 5/2002 | Petty et al. | |
| 6,767,982 B2 | 7/2004 | Standke et al. | |
| 6,780,955 B2 | 8/2004 | Barfurth et al. | |
| 6,864,323 B2 | 3/2005 | Schlosser et al. | |
| 7,781,520 B2 | 8/2010 | Standke et al. | |
| 8,236,918 B2 | 8/2012 | Mueh et al. | |
| 8,431,646 B2 | 4/2013 | Giessler-Blank et al. | |
| 8,795,784 B2 | 8/2014 | Standke et al. | |
| 2002/0090316 A1* | 7/2002 | Standke et al. ................... 422/1 |
| 2003/0166817 A1* | 9/2003 | Barfurth et al. ................ 528/10 |
| 2009/0005518 A1 | 1/2009 | Just et al. | |
| 2011/0144278 A1 | 6/2011 | Weissenbach et al. | |
| 2011/0282024 A1 | 11/2011 | Weissenbach et al. | |
| 2013/0253144 A1 | 9/2013 | Weissenbach et al. | |

FOREIGN PATENT DOCUMENTS

| | | |
|---|---|---|
| CN | 1769323 | 5/2006 |
| EP | 0 518 057 A1 | 5/1992 |
| EP | 1 205 481 A2 | 9/2001 |
| EP | 1 331 238 A2 | 1/2003 |
| EP | 1 331 238 A3 | 1/2003 |
| JP | 10-298289 | 11/1998 |
| JP | 2002-513427 | 5/2002 |
| JP | 2004-099872 | 4/2004 |
| JP | 4489381 | 4/2010 |
| RU | 1208791 | 10/1993 |
| RU | 2387677 | 4/2010 |
| WO | WO 2013/076035 A1 | 5/2013 |
| WO | WO 2013/076036 A1 | 5/2013 |

OTHER PUBLICATIONS

U.S. Appl. No. 14/360,114, filed May 22, 2014, Standke, et al.
U.S. Appl. No. 14/360,127, filed May 22, 2014, Standke, et al.
International Search Report issued Mar. 21, 2013 in PCT/EP2012/072964.
Office Action issued Aug. 28, 2015 in Chinese Patent Application No. 201280067724.7 (English translation).
Office Action issued Aug. 17, 2016 in Japanese Patent Application No. 2014-542786 (with English translation).
Office Action dated Aug. 28, 2015 in Chinese Patent Application No. 201280067724.7 (English translation).
Office Action dated Aug. 17, 2016 in Japanese Patent Application No. 2014-542786 (with English translation).

\* cited by examiner

*Primary Examiner* — Pancham Bakshi

(74) *Attorney, Agent, or Firm* — Oblon, McClelland, Maier & Neustadt, L.L.P.

(57) ABSTRACT

The invention relates to a composition comprising olefinically functionalized siloxane oligomers derived from olefinically functionalized alkoxysilanes and optionally alkoxysilanes functionalized with saturated hydrocarbons, and also, optionally, a tetraalkoxysilane, which have not more than one olefinic radical on the silicon atom, and whose chloride content is reduced, and also to processes for preparing them and to the use thereof.

18 Claims, No Drawings

LOW CHLORIDE COMPOSITIONS OF OLEFINICALLY FUNCTIONALISED SILOXANE OLIGOMERS BASED ON ALKOXYSILANES

CROSS REFERENCE TO RELATED APPLICATION

This application is a 371 of PCT/EP2012/072964, filed on Nov. 19, 2012, and claims priority to German Patent Application 10 2011 086 865.8, filed on Nov. 22, 2011.

The present invention relates to selected compositions of olefinically functionalized siloxane oligomers which are derived from olefinically functionalized alkoxysilanes, which may be present as a mixture of olefinically functionalized siloxane oligomers, which have not more than one olefinic radical per silicon atom, have a defined molecular weight and have a particularly low chloride content, and also to processes for preparing them and to the use thereof.

It is long-established practice to use mixtures of catenary and cyclic siloxane oligomers in the production of thermoplastics and of elastomers. Increasingly now, however, efforts are made to work in as low-VOC a way as possible, for example in the crosslinking of thermoplastics and also of elastomers, particularly in the production of cables (VOC—Volatile Organic Compounds).

It is also established practice to react vinyltriethoxysilane, optionally in mixtures with alkyltriethoxysilanes and/or tetraethoxysilane, by acidic HCl catalysed hydrolysis and condensation in an alcohol, in the presence of a calculated quantity of water. The alcohol is subsequently removed.

The acid used remains in the product or, in the case of the hydrochloride or hydrogen chloride (HCl), must be removed from the crude products again, at cost and inconvenience, after the reaction of the organofunctional alkoxysilanes, so as not to contribute to corrosion of the metallic surfaces of the processing machinery. This is done by distillation of the crude siloxane products.

In the application, such as in the production of filled cable compounds, for example, the oligomers are generally employed together with polymers and functional fillers in compounding machines. In the case of batch processes, this takes place in internal mixers or on mixing rolls, and, in the case of continuous compounding operations, it takes place in twin-screw extruders or co-kneaders. The typical processing temperatures here are in the 130-270° C. range; accordingly, at the points where the silane compound is added—depending on process, this is the inlet of the compounding machine or the polymer melt—as an inevitable result of the process, temperatures prevail which are above the boiling temperature of the silane monomers and distillable oligomers. Experience teaches that in addition to the unwanted loss of active substance, there is also increased incidence of deposition of free silane compounds on the internal housing walls or on the devolatilizing zones. These deposits are based on products of degradation of the vaporized silanes or distillable oligomers. Critical situations may arise as a result of these possibly alcohol-containing vapours, which in the case of backwards devolatilizing may enter the intake area and may come into contact with hot surfaces. This challenge also applies in part-filled zones of the compounding assemblies, or in their devolatilizing zones. Overall, for these reasons, the compounds used must have a very high flash point. Account must also be taken of the liberated hydrolysis alcohol, which is produced, in the case of filled polymer compounds, during the hydrolysis reaction of the ester groups of the silicon-functional group of the silane or silane oligomer in the compound. Overall, therefore, reducing the VOC (volatile organic compounds) is a very important criterion with this technology.

As already mentioned, the customary operating temperatures for the compounding operation are usually above 101° C., and kneading, for example, takes place frequently at 170 to 180° C. Consequently there continues to be a requirement for reduced-VOC and low-corrosion oligomers which as far as possible no longer contain any acidic compounds, such as formic acid, HCl or Cl-containing compounds. Even minuscule amounts of these compounds lead to corrosion at the stated operating temperatures, and hence to wear of the machine components after brief downtime periods. For stainless steels, nickel-based alloys and copper-based alloys, for instance, it is said that they are not resistant, owing to the corrosion that occurs, with respect to formic acid or HCl (see, for example, Handbuch der Metallbeläge, Witzemann, January 2010, Section 7.2 Corrosion Resistance, pp. 200-238). In a brochure (Chemische Beständigkeit der Nirosta®-Stähle, ThyssenKrupp Nirosta GmbH, Edition 3, January 2008), ThyssenKrupp describes various types of corrosion and names typical triggers for erosive surface corrosion in the form of perforation corrosion, gap corrosion or stress crack corrosion, such as the presence of acids and chloride ions. The corrosive effect of acids and chloride ions increases markedly with elevated temperature. The removal of mass from unalloyed steels at high atmospheric humidity (80 to 100% relative humidity) in the presence of formic acid may amount to 10 g/m$^2$, and in the presence of chlorides may amount to up to 105 g/m$^2$, after 14 days. Accordingly, the amount of hydrolysis and condensation catalysts in the oligomers prepared in accordance with the invention is as far as possible to be reduced down to a level in the weight ppm to weight ppt range or down to the detection limit.

As well as the corrosion during processing, however, an important part is also played by the presence of chloride/chloride ions or acids in the end application, e.g. in cable insulation systems. As well as the possible corrosion on the insulated current conductor, and the possible negative effect on the electrical properties of the cable insulation itself, it is absolutely necessary to avoid corrosive and halogen-containing combustion gases in the case of halogen-free compounds containing flame retardants. This requirement applies, of course, to all raw materials employed in these compounds.

Through the aforesaid avoidance or minimization of the chloride fractions and acid fractions in the siloxane oligomers of the invention, it would be possible to meet these challenges in full.

Moreover, increasing interest is being focused on silane systems which contain increasingly less organic solvent and therefore are more eco-friendly. For this reason, the trend is toward providing precondensed, lower-VOC silane systems, which then, however, must be stabilized, since they still contain the catalyst, or from which the catalyst must be removed, in a costly and inconvenient procedure.

EP 0 518 057 B1 and U.S. Pat. No. 5,282,998 disclose a process for preparing mixtures of catenary and cyclic siloxane oligomers. According to Examples 1 and 6, the respective product mixtures are prepared by hydrolysis and condensation of vinyltrialkoxysilanes, or of a mixture of vinyl- and alkyltrialkoxysilanes, the hydrolysis and condensation being carried out using 0.63 mol of water per mole of Si in the silane employed. With the method disclosed therein, moreover, the HCl catalyst cannot be fully removed, and a corrosive residue amounting to about 50 to about 230 ppm of HCl remains even in products distilled in accordance with the process disclosed. On ingress of moisture or as a result of progressive condensation, because of the presence of HCl in the oligomer mixture, alcohol may be released. If such a release of alcohol occurs during the storage of the oligomer mixture, this generally leads to an unwanted fall in the flash point. For this reason, a product must be subjected to purifying distillation to diminish the HCl content under reduced pressure in an energy-intensive and inconvenient procedure during the actual work-up stage, in accordance with EP 0 518 057 B1. Said oligomer mixtures find application as crosslinking agents for thermoplastic polyolefins by graft polymerization and hydrolytic condensation.

U.S. Pat. No. 6,395,856 B1 discloses the hydrosilylation of oligomers containing organofunctional silicon, such as the hydrosilylation of vinylmethoxysiliconates from the reaction of vinyltrimethoxysilane in the presence of formic acid, under inert gas, without presence of a diluent.

CN 100343311 C describes silane oligomers obtained by catalytic hydrolysis and condensation of vinyltrimethoxysilane. The use of metal salt catalysts, such as copper hydroxide, for example, in combination with acids is mandatory. The removal of the catalysts is costly and inconvenient and it is therefore likely that catalyst residues and/or neutralization products remain in the product and have deleterious effects in numerous applications. Here, accordingly, the removal of the acid by a calcium carbonate neutralization and filtration of the resultant calcium salt is disclosed.

In the prior art, for a number of siloxane oligomers, the flash point drops within a few days in the course of storage to below 50° C., owing to possibly excessive concentrations of catalyst residues that remain in the composition. Other compositions from the prior art, in turn, exhibit excessive mass losses of up to 25 wt % at 150° C., and a large mass loss of around 50 to 90 wt % at 200° C.

Siloxanes with high molecular weights in the 10 000 g/mol region are described in JP10 298289 A, these siloxanes being prepared by hydrolysis and precondensation or condensation of a vinyl- or phenyl-functional alkoxysilane in the presence of an acid catalyst, the catalyst being subsequently removed from the product mixture by means of an anhydrous, anionic ion exchanger. In the majority of applications, material of such high molecular weight cannot be used, owing to high viscosities and inadequate reactivity.

Organosiloxane oligomers having a multiplicity of possible functionalities, an average molecular weight in the range of Mn=350-2500 g/mol, and a polydispersity (D=Mw/Mn) of 1.0-1.3 are described in JP2004 099872. The preparation takes place in the presence of a basic catalyst from a very diluted aqueous solution with a very low, economically unproductive space-time yield; accordingly, 1 l of solution yielded 1 ml of isolated product. The teaching of JP2004 099872A could not be reproduced in the manner disclosed. For instance, a number of times, Example 1 could not be reproduced in the manner indicated.

It was an object of the present invention to provide further, particularly low-chlorine mixtures of purely olefinic siloxane oligomers, based more particularly on alkenylalkoxysilanes, and particularly low-chlorine mixtures of olefinically and alkyl-functionalized siloxane oligomers, based more particularly on alkenyl-/alkyl-alkoxysilanes, and also a process for preparing such mixtures. Of further concern was as far as possible, using the siloxane oligomers modified in accordance with the invention, to obtain an improvement in processing properties with thermoplastics or elastomers, and also in the performance of the thermoplastics or elastomers produced accordingly. A key point with regard to processability is also the rapid dispersibility of the siloxane oligomers in the thermoplastics, in combination with extremely low losses of mass at the prevailing temperatures in extruder applications. In accordance with the invention the aim was to achieve a further significant reduction, in accordance with the process, in the chlorine content, more particularly the total chloride content and/or else the hydrolysable chloride content. Moreover, the siloxane oligomers prepared by the process were to have very high flash points, to be deemed low-VOC even at high temperatures, and to be useful in the practical art at elevated temperatures without further safety measures. The siloxane oligomers themselves, as well, are to exhibit only small losses in mass even at high temperatures, such as in extruders, for example. As further objects, the olefinic siloxane oligomers were to have good stability in storage even over prolonged storage periods, and also, preferably, any increase in the viscosity of the mixture over a prolonged time period was to be avoided, as a result of gelling or flocculation or post-condensation, for example.

The objects are achieved in accordance with the independent claims; preferred embodiments are set out in the dependent claims and in the description in detail.

Surprisingly it has been found that olefinically functionalized alkoxysilanes and optionally alkylalkoxysilane and optionally tetraalkoxysilane can be converted in a simple and economic way by reaction with a defined amount of water, more particularly of greater than or equal to 0.5 to 1.5 mol of water per mole of silicon atoms in the alkoxysilanes used, and optionally in the presence of a solvent, preferably alcohol, to give compositions of particularly low-chlorine olefinic siloxane oligomers, if the hydrolysis alcohol and the solvent, where present, are substantially removed, in particular with only the solvent and/or the hydrolysis alcohol being removed by distillation, and if at least once during the distillative work-up or subsequently a further defined amount of alcohol is added and removal is carried out, more particularly with distillative removal of the alcohol.

It was surprising that the siloxane oligomers obtained in this way, in the form simply of the liquid-phase product, exhibit a very low chloride content and total chloride content. In accordance with the invention, the resulting compositions have a particularly low chlorine content and a particularly low monomer content—preferably there are no longer any monomers detectable. The process of the invention is particularly economic since now only the low-boiling solvents are removed by distillation, more particularly the added alcohol and/or hydrolysis alcohol. Advantageously, the high-boiling liquid-phase product itself is no longer distilled. Moreover, in compositions according to the invention, it has been possible to increase the amount of T structures and the molecular weight. A further improvement has also been possible in the stability of said compositions, more particularly the stability of quality.

In contrast to the known oligomers, the compositions of the invention and the olefinically functionalized siloxane oligomer compositions prepared by the process of the invention do not require further work-up, such as distillation of the compositions of the siloxane oligomers, for example. The compositions prepared by the process of the invention, the oligomeric liquid-phase product, gives the same or better performance than known olefinic siloxane oligomers purified, nevertheless, by means of distillation. In accordance with the invention, therefore, the resulting siloxane oligomer need no longer be itself distilled, but can instead be obtained and used purely as the liquid-phase product.

In accordance with the invention, moreover, acidic catalysts which are gaseous under standard conditions, more particularly HCl, are used as hydrolysis and/or condensation catalysts, and may be dissolved in the aqueous or alcoholic phase. A reaction therefore takes place under the conditions of homogeneous catalysis. A surprising advantage was that as a result of the process of the invention, the gaseous catalyst can be removed virtually entirely from the compositions.

The invention provides a process for preparing a composition of the invention and to compositions obtainable by this process, comprising olefinically functionalized siloxane oligomers which have not more than one olefinic radical on the silicon atom, the olefinically functionalized siloxane oligomers comprise Si—O-crosslinked structural elements which form catenary, cyclic, crosslinked and/or three-dimensionally crosslinked structures, with at least one structure corresponding in idealized form to the general formula I, $$(R^1O)[(R^1O)_{1-x}(R^2)_x(A)O]_a[Si(Y)_2O]_c[Si(B)(R^4)_y(OR^3)_{1-y}O]_bR^3 \quad (I),$$

the structural elements being derived from alkoxysilanes and

A in the structural element corresponds to an olefinic radical, more particularly having 2 to 16 C atoms, and B in the structural element corresponds in particular to a linear, branched or cyclic saturated hydrocarbon radical having 1 to 16 C atoms, preferably to a linear, branched or cyclic alkyl radical having 1 to 16 C atoms, Y corresponds to $OR^3$ or, in crosslinked structures, independently at each occurrence, to $OR^3$ or $O_{1/2}$, and in three-dimensionally crosslinked structures, Y corresponds independently at each occurrence to $OR^3$ or $O_{1/2}$, where $R^1$ independently at each occurrence corresponds to a linear, branched and/or cyclic alkyl radical having 1 to 4 C atoms, and optionally to H, $R^3$ independently at each occurrence corresponds to a linear, branched and/or cyclic alkyl radical having 1 to 4 C atoms, and optionally to H, and $R^2$ independently at each occurrence corresponds to a linear, branched or cyclic alkyl radical having 1 to 15 C atoms and $R^4$ corresponds independently at each occurrence to a linear, branched or cyclic alkyl radical having 1 to 15 C atoms, a, b, c, x and y independently correspond to integers with $1 \leq a$, $0 \leq b$, $0 \leq c$, x independently at each occurrence is 0 or 1, y independently at each occurrence is 0 or 1, and $(a+b+c) \geq 2$, more preferably $x=0$ and $y=0$, where in particular the total chloride content is less than or equal to 100 mg/kg, optionally to 0 mg/kg, more particularly less than or equal to 75 mg/kg, preferably less than or equal to 50 mg/kg, more preferably less than or equal to 45 mg/kg, very preferably less than or equal to 40 mg/kg, preferably less than or equal to 20 mg/kg, more preferably less than or equal to 10 mg/kg, with further preference less than or equal to 5 mg/kg to 0 mg/kg, and in particular, additionally, the hydrolysable chloride content is less than 20 mg/kg, more particularly less than or equal to 10 mg/kg, preferably less than or equal to 5 mg/kg to 0 mg/kg, more particularly in the composition as liquid-phase product, and, more particularly, the weight-average molecular weight (Mw) is greater than or equal to 410 g/mol to 580 g/mol and the number-average molecular weight (Mn) is greater than or equal to 370 to 470 g/mol, with the polydispersity, as the ratio of Mw/Mn, being 1.00 to 1.25, where the structural elements of the olefinically functionalized siloxane oligomers $[(R^1O)_{1-x}(R^2)_xSi(A)O]_a$, $[Si(B)(R^4)_y(OR^3)_{1-y}O]_b$ and $[Si(Y)_2O]_c$ in the general formula I together are present, in relation to all silicon atoms of the general formula I, at greater than or equal to 3% as T structure and preferably less than 10% as T structure.

According to one particularly preferred embodiment, the weight-average molecular weight (Mw) is greater than or equal to 430 to 550 g/mol, more particularly 450 to 530 g/mol; mention may further be made of the relevant numerical values 415, 420, 425, 435, 440, 445, 455, 460, 465, 470, 475, 480, 485, 490, 495, 500, 505, 510, 515, 520, 525, 535, 540, 545, 555, 560, 565, 570 and 575 g/mol, and likewise with particular preference the number-average molecular weight (Mn) is in the range from 390 g/mol to 450 g/mol, more particularly 400 to 435 g/mol; mention may further be made of the relevant numerical values 375, 380, 385, 395, 405, 410, 415, 420, 425, 430, 440, 445, 455, 460 and 465 g/mol, the polydispersity, as the ratio of Mw/Mn being preferably 1.00 to 1.25. It is further preferred if the polydispersity is in the range from 1.01 to 1.24 including all values in between, more particularly including 1.01, 1.02, 1.03, 1.04, 1.05, 1.06, 1.07, 1.08, 1.09, 1.1, 1.11, 1.12, 1.13, 1.14, 1.15, 1.16, 1.17, 1.18, 1.19, 1.2, 1.21, 1.22, 1.23.

Weight-average molecular weight (Mw)

$$M_w = \frac{\sum n_i M_i^2}{\sum n_i M_i}$$

and number-average molecular weight (Mn)

$$M_n = \frac{\sum n_i M_i}{\sum n_i}$$

in each case with $n_i$=amount of substance [mass] of the i-mer, $M_i$=molar mass of the i-mer. Details relating to the definition of weight average and number average, which are known per se to the skilled person, may also be found by the reader, alternatively, from sources including the Internet at http://de.wikipedia.org/wiki/Molmassenverteilung, or from a standard work of mathematics. It is generally the case that the designation disiloxane, trisiloxane, tetrasiloxane, pentasiloxane covers the siloxanes that are linear and/or branched in each case, and cyclotrisiloxane, cyclotetrasiloxane, cyclopenta- or cycloheptasiloxane covers the cyclic siloxanes.

Further provided by the invention is a composition comprising olefinically functionalized siloxane oligomers in which the structural elements $[(R^1O)_{1-x}(R^2)_xSi(A)O]_a$, $[Si(B)(R^4)_y(OR^3)_{1-y}O]_b$ and $[Si(Y)_2O]_c$ in the general formula I together are present, in relation to all silicon atoms of the general formula I, preferably at greater than or equal to 4%, more preferably at greater than or equal to 5%, such as 5% to 10%, more preferably still at greater than or equal to 7.5%, with further preference at greater than or equal to 10%, at greater than or equal to 11%, at greater than or equal to 13%, at greater than or equal to 15%, alternatively at greater than or equal to 20% or, according to a further alternative, at greater than or equal to 25%.

According to one alternative, the structural elements $[(R^1O)_{1-x}(R^2)_xSi(A)O]_a$, $[Si(B)(R^4)_y(OR^3)_{1-y}O]_b$ and $[Si(Y)_2O]_c$, may be present all in all, i.e. in total, in the general formula I together, in relation to all silicon atoms of the general formula I, at greater than or equal to 5% as T structure, with the proviso that 1≤a, 0≤b, 0≤c and (a+b+c)≥2 or, alternatively, that in total the structural elements $[(R^1O)_{1-x}(R^2)_xSi(A)O]_a$ are present, in relation to the sum total of silicon atoms in the general formula I, at greater than or equal to 5% as T structure, such as 5% to 10%, more particularly at greater than or equal to 7.5%, preferably at greater than or equal to 10%, more preferably at greater than or equal to 11%, with further preference at greater than or equal to 13%, at greater than or equal to 15%, alternatively at greater than or equal to 20% or, according to a further alternative, at greater than or equal to 25%.

Likewise provided by the invention is a composition comprising olefinically functionalized siloxane oligomers in which the amount of silicon atoms of monomeric alkoxysilanes is less than or equal to 3%, more particularly down to the detection limit or 0.0%, in relation to all silicon atoms of the siloxane oligomers, more particularly in relation to the silicon atoms of the general formula I, with the proviso that 1≤a, 0≤b, c and (a+b+c)≥2, the monomers content being preferably less than or equal to 2%, more preferably less than or equal to 1%, with particular preference the amount is less than or equal to 0.75% to 0 wt %, likewise preferably less than or equal to 0.5%.

Additionally provided by the invention is a composition comprising olefinically functionalized siloxane oligomers in which the structural elements $[(R^1O)_{1-x}(R^2)_xSi(A)O]_a$, $[Si(B)(R^4)_y(OR^3)_{1-y}O]_b$ and $[Si(Y)_2O]_c$ in the general formula I together, in relation to all silicon atoms of the general formula I, are present at greater than or equal to 1% as T structure, more particularly at greater than or equal to 2%, preferably at greater than or equal to 3%, greater than or equal to 4%, more preferably at greater than or equal to 5%, such as 5% to 10%, more preferably at greater than or equal to 7.5%, with further preference at greater than or equal to 10%, at greater than or equal to 11%, at greater than or equal to 13%, at greater than or equal to 15%, alternatively at greater than or equal to 20%, or, according to a further alternative, at greater than or equal to 25%.

According to one alternative, the structural elements $[(R^1O)_{1-x}(R^2)_xSi(A)O]_a$, $[Si(B)(R^4)_y(OR^3)_{1-y}O]_b$ and $[Si(Y)_2O]_c$, may be present all in all, i.e. in total, in the general formula I together, in relation to all silicon atoms of the general formula I, at greater than or equal to 5% as T structure, with the proviso that 1≤a, 0≤b, 0≤c and (a+b+c)≥2 or, alternatively, that in total the structural elements $[(R^1O)_{1-x}(R^2)_xSi(A)O]_a$ are present, in relation to the sum total of silicon atoms in the general formula I, at greater than or equal to 5% as T structure, such as 5% to 10%, more particularly at greater than or equal to 7.5%, preferably at greater than or equal to 10%, more preferably at greater than or equal to 11%, with further preference at greater than or equal to 13%, at greater than or equal to 15%, alternatively at greater than or equal to 20% or, according to a further alternative, at greater than or equal to 25%.

The invention provides a composition comprising olefinically functionalized siloxane oligomers which have not more than one olefinic radical on the silicon atom, and the olefinically functionalized siloxane oligomers comprise Si—O-crosslinked structural elements which form catenary, cyclic, crosslinked and/or three-dimensionally crosslinked structures, with at least one structure corresponding in idealized form to the general formula I, the siloxane oligomers having derived structural elements from at least one of the alkoxysilanes, (i) from olefinically functionalized alkoxysilanes of the general formula II,

$$A-Si(R^2)_x(OR^1)_{3-x} \tag{II}$$

where A corresponds to an olefinic radical, with $R^2$ and x as defined above, x preferably being 0, and $R^1$ independently corresponding to a linear, branched and/or cyclic alkyl radical having 1 to 4 C atoms, or optionally a mixture of alkoxysilanes of the formula II, and (i.1) optionally from alkoxysilane of the formula III functionalized with (at least) one saturated hydrocarbon radical,

$$B-Si(R^4)_y(OR^3)_{3-y} \tag{III}$$

where B corresponds to an unsubstituted hydrocarbon radical, with $R^3$, $R^4$ and y as defined above, y being preferably 0, or optionally a mixture of alkoxysilanes of the formula III, and (i.2) optionally from (at least) one tetraalkoxysilane of the general formula IV as $Si(OR^3)_4$ with $R^3$ independently at each occurrence as defined above, the chlorine content, more particularly total chloride content, being preferably less than or equal to 100 mg/kg, more particularly less than or equal to 75 mg/kg to 0 mg/kg, more preferably less than or equal to 50 mg/kg, and the structural elements being preferably present together, in relation to all silicon atoms of the siloxane oligomer, at greater than or equal to 1% as T structure, preferably at greater than or equal to 2%, greater than or equal to 3%, greater than or equal to 5%, such as 5% to 10%, more particularly at greater than or equal to 7.5%, preferably at greater than or equal to 10%, more preferably at greater than or equal to 11%, with further preference at greater than or equal to 13%, at greater than or equal to 15%, alternatively at greater than or equal to 20% or, according to a further alternative, at greater than or equal to 25%. With particular preference x=0 and y=0.

All alkyl radicals, such as $R^1$, $R^2$, $R^3$ and $R^4$, having 1 to 4 C atoms may in each case independently of one another be preferably methyl, ethyl, propyl, n-propyl, isopropyl, butyl, n-butyl, isobutyl, tert-butyl and/or 2-methylbutyl. The alkyl radicals $R^2$ and/or $R^4$ here may, in each case independently, correspond to a linear, branched or cyclic alkyl radical having 1 to 15 C atoms, such as methyl, ethyl, propyl, n-propyl, isopropyl, butyl, n-butyl, isobutyl, tert-butyl or, with 5 C atoms, 2-methylbutyl, n-pentyl, n-hexyl, n-heptyl, n-octyl, n-nonyl, n-decyl, n-undecyl, etc., and also the corresponding iso-alkyls and also cyclopentyl, cyclohexyl and also alkyl-substituted cyclopentyl and cyclohexyl groups. The alkyl radicals $R^2$ and $R^4$ here may be selected, in each case independently, from a methyl, ethyl, propyl, butyl, isobutyl, n-butyl, tert-butyl, pentyl, n-pentyl, isopentyl, neopentyl, hexyl, isohexyl, neohexyl, 2,2-dimethylbutyl, 2,3-dimethylbutyl, 2-methylpentyl, 3-methylpentyl, octyl, n-octyl, isooctyl, nonyl, decyl, undecyl, dodecyl, $C_{13}H_{27}$, $C_{14}H_{29}$ and $C_{15}H_{31}$ group.

Siloxane oligomers and also the alkoxysilanes of the formulae II, III and IV may be used or isolated as products of transesterification. For example, as methoxydiethoxyalkylsilane or methoxydiethoxyvinylsilane.

According to particularly preferred embodiments, the olefinic radical A in formulae I and/or II corresponds to a non-hydrolysable olefinic radical, more particularly to a linear, branched or cyclic, alkenyl- or cycloalkenyl-alkylene-functional group having in each case 2 to 16 C atoms, preferably having 2 to 8 C atoms, more preferably a vinyl, allyl, butenyl, such as 3-butenyl, pentenyl, hexenyl, ethylhexenyl, heptenyl, octenyl, cyclohexenyl-C1 to C8-alkylene, preferably cyclohexenyl-2-ethylene, such as 3'-cyclohexenyl-2-ethylene and/or cyclohexadienyl-C1 to C8-alkylene, preferably cyclohexadienyl-2-ethylene group.

Also preferably the unsubstituted hydrocarbon radical B, independently in formulae I and/or III, may correspond to a linear, branched or cyclic alkyl radical having 1 to 16 C atoms, more particularly a methyl, ethyl, propyl, isobutyl, octyl, or hexadecyl group.

According to one alternative, the olefinically functionalized siloxane oligomers, especially of the formula I, may preferably have a ratio of silicon atoms to A radicals and B radicals, with the proviso that a is greater than or equal to 1, b is greater than or equal to 0 and c is greater than or equal to 0, and (a+b+c) is greater than or equal to 2, of Si to (A radicals+B radicals) of 1:1 to about 1.22:1, preferably of 1:1 to 1.15:1.

Likewise provided by the invention are processes in which compositions comprising siloxane oligomers are obtained and compositions comprising olefinically functionalized siloxane oligomers which have not more than one olefinic radical on the silicon atom and in which, in particular in each case independently, (i) the structural element $[(R^1O)_{1-x}(R^2)_xSi(A)O]_a$ in the general formula I, in relation to all silicon atoms of the general formula I, is prepared at greater than or equal to 1% as T structure, more particularly at greater than or equal to 2%, at greater than or equal to 3%, preferably at greater than or equal to 4%, more preferably at greater than or equal to 5%, alternatively at greater than or equal to 7.5% or, according to a further alternative, at greater than or equal to 8%, preferably to less than 10%, more preferably less than 9.5%, and optionally (ii) the structural elements $[(R^1O)_{1-x}(R^2)_xSi(A)O]_a$ and $[Si(B)(R^4)_y(OR^3)_{1-y}O]_b$ and $[Si(Y)_2O]_c$ in the general formula I, in each case independently of one another, together, in relation to all silicon atoms of the general formula I, are prepared at greater than or equal to 20% as D structure, more particularly at greater than or equal to 25%, preferably at greater than or equal to 30%, more preferably at greater than or equal to 35%, 40% or else at 45%, and preferably less than 55%, more particularly for a greater than or equal to 1, b greater than or equal to 0, c greater than or equal to 0, preferably a greater than or equal to 1 and b=0, c=0 or a greater than or equal to 1 and b greater than or equal to 1 and c is 0, or, in each case independently, a, b and c greater than or equal to 1, and optionally (iii) the structural element $[(R^1O)_{1-x}(R^2)_xSi(A)O]_a$ in the general formula I, in relation to all silicon atoms of the general formula I, is prepared at less than or equal to 60% as M structure, more particularly at less than or equal to 55%, preferably at less than or equal to 50%, more preferably less than or equal to 45%, and preferably greater than 30%, more particularly greater than or equal to, and optionally (iv.a) the structural element $[Si(B)(R^4)_y(OR^3)_{1-y}O]_b$ in the general formula I, in relation to all silicon atoms of the general formula I, is prepared at less than or equal to 45% as M structure, more particularly at less than or equal to 40%, preferably at less than or equal to 38%, preferably greater than 30%, and/or optionally (iv.b) the structural element $[Si(B)(R^4)_y(OR^3)_{1-y}O]_b$ in the general formula I is prepared at greater than or equal to 10% as M structure, more particularly at greater than or equal to 20%, more particularly at greater than or equal to 25%, preferably at greater than or equal to 30%, and/or optionally (v) the structural element $[Si(Y)_2O]_c$ in the general formula I is prepared preferably between 15% to 52% as D structure, or is prepared predominantly as D structure, alternatively more than 20% of the structural elements $[Si(Y)_2O]_c$ in the general formula I are present as D structure, more particularly more than 25%, preferably more than 30%, more preferably more than 35%.

According to one particularly preferred alternative, a purely olefinic siloxane oligomer prepared, more particularly with the structural elements $[(R^1O)_{1-x}(R^2)_xSi(A)O]_a$ in the general formula I, has at 38% to 60% M structures, at 35% to 55% D structures and at greater than or equal to 3% T structures, more particularly greater than 3.5% T structures.

The amount of M, D, T or Q structures is determined by a method known to the skilled person, such as, preferably, by means of $^{29}$Si NMR.

The definition of M, D, T and Q structures refers generally to the number of oxygens bonded in siloxane compounds, as illustrated below for alkoxysilyl units by way of example: with R independently at each occurrence being $OR^1$, $OR^3$, group A or group B, as defined above. With $M=[-O_{1/2}—Si(R)_3]$, $D=[-O_{1/2}—Si(R)_2—O_{1/2}—]$, $T=[RSi(—O_{1/2}—)_3]$ and $Q=[Si(—O_{1/2}—)_4]$. $—O_{1/2}—$ is always an oxygen in a siloxane bond. Accordingly, in order to be able to give a clearer description of silicones and siloxanes or silane oligomers, it is possible, rather than an idealized formulaic description, also to employ the M, D, T (crosslinked) and Q (three-dimensionally crosslinked) structures. For the more precise nomenclature of the designation of such siloxane structures, reference may be made to Römpp Chemielexikon—entry heading: Silicones. From structural units M, for example, it is only possible to form dimers with $M_2$, such as hexaalkoxydisiloxane. The construction of chains requires compositions of structural units D and M, giving trimers ($M_2D$, octaalkoxytrisiloxane), tetramers ($M_2D_2$) and so on up to linear oligomers with $M_2D_n$ can be constructed. The formation of cyclic oligomers requires structural units D. In this way, for example, rings with $D_3$, $D_4$, $D_5$ or higher can be constructed. Branched and/or crosslinked structural elements, under which spiro compounds should also be reckoned, are obtained when structural units T and/or Q are present together. Conceivable crosslinked structures may be present in the form of $T_n$ (n≥4), $D_nT_m$ (m<n), $D_nT_m$ (n>>m), $D_3T_2$, $M_4Q$, $D_4Q$ and so on, to give just a few conceivable possibilities. Structural units M are also referred to as stoppers or transfer agents, while D units are termed chain formers or ring formers, and the T, and possibly also Q, units are referred to as network formers. Thus the use of tetraalkoxysilanes, because of the four hydrolysable groups, and ingress of water and/or moisture, can bring about structural units Q and hence the formation of a network (three-dimensionally crosslinked). In contrast, fully hydrolysed trialkoxysilanes may give rise to branches, i.e. T units $[—Si(—O—)_{3/2}]$, in a structural element, as for example $MD_3TM_2$ for an oligomer having a degree of oligomerization of n=7, the respective functionalities on the free valencies of the silyloxy units requiring definition in these structural representations.

Further details on the nomenclature comprehension of M, D, T and Q structures, and also relevant methods of analysis, include the following:

"Strukturuntersuchungen von oligomeren und polymeren Siloxanen durch hochauflösende $^{29}$Si-Kernresonanz" [Structural analyses of oligomeric and polymeric siloxanes by high-resolution $^{29}$Si NMR], H. G. Horn, H. Ch. Marsmann, Die Makromolekulare Chemie 162 (1972), 255-267, "Über die $^1$H-, $^{13}$C- und $^{29}$Si-NMR chemischen Verschiebungen einiger linearer, verzweigter und cyclischer Methyl-Siloxan-Verbindungen" [On the $^1$H, $^{13}$C and $^{29}$Si NMR chemical shifts of certain linear, branched and cyclic methylsiloxane compounds], G. Engelhardt, H. Jancke, J. Organometal. Chem. 28 (1971), 293-300, "Chapter 8—NMR spectroscopy of organosilicon compounds", Elizabeth A. Williams, The Chemistry of Organic Silicon Compounds, 1989 John Wiley & Sons Ltd, 511-533.

In accordance with the process of the invention, compositions are obtained in which the ratio of M:D structures in the olefinic siloxane oligomers is preferably from 1:2 to 3.5:1, more particularly 1:2 to 2.5:1, alternatively 1:2 to 1.5:1, more particularly with a monomeric alkoxysilanes content of less than or equal to 3% to 0%, preferably of less than or equal to 2%, more preferably of less than or equal to 1%, with the amount of T structures in total being preferably greater than or equal to 1%, more preferably greater than or equal to 3%.

Compositions which have the aforementioned structures possess a stable degree of crosslinking, in view of the reduced amount of monomeric alkoxysilanes, and have a particularly low chlorine content. One noteworthy advantage of the compositions of the invention and of the process of the invention is that the olefinic siloxane oligomers prepared, more particularly the vinyl oligomers, differ from the known oligomers in requiring no further working-up, such as distillation of the compositions of the siloxane oligomers. The oligomeric liquid-phase product prepared gives the same performance or better than that of known siloxane oligomers purified, nevertheless, by distillation.

A particular advantage of the olefinically functionalized siloxane oligomers prepared in accordance with the invention is that the reduced chlorine content and the increased level of T structures in the siloxane oligomers directly improves the processing qualities of the siloxane oligomers with polymers, such as when kneading or compounding, for example. Specifically there is improvement in the melt index, thereby reducing the energy consumption in processing. Furthermore, the corrosion of the iron-containing machines goes down, since it has been possible to achieve a further reduction in the chloride content. Moreover, the water uptake capacity of the polymers compounded with the siloxane oligomers of the invention is reduced, and also, frequently, their elongation at break and usually the tensile strength are improved. The reduced water uptake capacity is advantageous in the subsequent application sectors, such as in the production of filled cable compounds, for example, especially for cables which are to be laid in the earth and are subject to persistent moisture.

It may be preferable for the composition and/or the siloxane oligomer also to have trialkylsilane groups, such as trimethylsilane or triethylsilane groups, as a result, for example, of the addition of alkoxytrialkylsilane, in order to adjust the degree of oligomerization.

In order to fulfil the stated objects, compositions obtained by the process of the invention are those of mixtures of olefinic siloxane oligomers in which, in particular, more than 20 wt % of the siloxane oligomers have a degree of oligomerization of greater than or equal to 4, optionally greater than or equal to 8; in other words, the number of silicon atoms (n) per oligomer is greater than or equal to 4, optionally greater than or equal to 8 (n≥8), and more preferably at the same time the fraction of siloxane oligomers with T structure is greater than or equal to (≥) 1%, more particularly greater than or equal to 2%, preferably greater than or equal to 3%, such as 3% to 10%, and at the same time the viscosity is preferably less than or equal to ≤3000 mPa s, more particularly less than or equal to 1000 mPa s and preferably greater than or equal to 5 mPa s, more preferably less than or equal to 500 mPa s and more particularly greater than or equal to 10 mPa s. Alternatively it is preferred if the viscosity of the composition comprising olefinically functionalized siloxanes is less than or equal to 3000 mPa s and greater than or equal to 7 mPa s, preferably less than or equal to 2500, more particularly less than or equal to 500 mPa s and greater than or equal to 10 mPa s, alternatively preferably less than or equal to 1000 mPa s, more particularly less than or equal to 500 mPa s and greater than or equal to 12 mPa s. Compositions of this kind can be outstandingly compounded with elastomers or thermoplastics, and feature the improved properties identified above.

Generally speaking, the siloxane oligomers may be linear and/or cyclic oligomers with M and D structures and T structure. Only on addition of tetraalkoxysilane during the preparation or before the processing of the oligomers are siloxane oligomers with M, D, Q and optionally T structures formed. Compositions of the invention comprise siloxane oligomers in which the sum of (a+b) is an integer greater than or equal to 2, more particularly greater than or equal to 4 to 30, preferably greater than or equal to 6 to 30, optionally greater than or equal to 8 to 30, and c is optionally greater than or equal to 1, such as 1 to 20, for example, more particularly 2 to 15. In the case of degrees of oligomerization that are too high, it is not possible to achieve homogeneous and reproducible product properties in the siloxane oligomers. For adjusting the degree of oligomerization during the preparation of the composition it may therefore be preferable, for chain termination at a desired point in time, to add an alkoxytrialkylsilane, such as an ethoxytrimethylsilane or methoxytrimethylsilane with preference, to the composition that is to be prepared.

The compositions obtained by the process of the invention may comprise at least 20 wt % of siloxane oligomers in which the degree of oligomerization in terms of olefinically functionalized siloxane oligomers is greater than or equal to 4, more particularly greater than 6, optionally greater than or equal to 8. It is further preferred here if for at least 20 wt % of the oligomers, more particularly of the formula I, the sum of (a+b) is an integer greater than or equal to 4, alternatively greater than or equal to 5, the sum of (a+b) being more particularly greater than or equal to 6, optionally greater than or equal to 8, with a greater than or equal to 1 and b equal to 0 or b greater than or equal to 1, preferably a and b each independently of one another being greater than or equal to 2, preferably greater than or equal to 3, more particularly independently greater than or equal to 4, and optionally with c in (a+b+c) being greater than or equal to 1. According to one preferred alternative or in addition to the aforementioned features, 95% to 100% of the siloxane oligomers have a degree of oligomerization of 2 to 20, preferably from 2 to 6, alternatively 2 to 7, preferably from 3 to 10.

According to a preferred alternative, b is greater than or equal to 1, more particularly greater than or equal to 2, preferably greater than or equal to 4. With further preference, at least 20% of the olefinically functionalized siloxane oligomers, especially of the formula I, have a degree of oligomerization (a+b+c) of greater than or equal to 4, optionally greater than or equal to 8, with a greater than or equal to 1 and b greater than or equal to 1 and optionally c greater than or equal to 1, where the fraction of siloxane oligomers with T structure is greater than or equal to (≥) 1%, and preferably the viscosity is less than or equal to ≤1000 mPa s and more particularly greater than 5 mPa s. With further preference, the fraction of T structures in the siloxane oligomers is greater than or equal to 3%, alternatively greater than or equal to 1% to 10%, and at the same time the viscosity is less than or equal to 500 mPa s.

The compositions obtained according to an alternative procedure additionally or alternatively to one or more of the aforementioned features have, preferably after complete hydrolysis of all the alkoxy groups, an alcohol content of less than or equal to 20 wt %, more particularly less than or equal to 18 wt %, preferably less than or equal to 16 wt %, more preferably less than or equal to 15 wt % to less than or equal to 0.1 wt %, likewise preferably less than or equal to 12 wt % to less than or equal to 1 wt %, with the proviso that the amount of water added is only that needed for the hydrolysis. There is no further dilution for the determination.

Additionally or alternatively to one or more of the aforementioned features, the composition obtained by the process preferably has a molar ratio of A radicals to B radicals of 1:0 to 1:8, preferably of about 1:0 to 1:4, more preferably a ratio of 1:0 to 1:2, preferably 1:0 to 1:1, more preferably of 1:1.

It is further preferred here if the composition obtained by the process comprises olefinic siloxane oligomers in which (i) the ratio of the silicon atoms, selected from olefinically functionalized silicon atoms and from silicon atoms functionalized with a saturated hydrocarbon, to alkoxy groups in the siloxane oligomer or optionally in the general formula I is from 1:0.3, to 1:3.5, more particularly 1:0.3 to 1:2.0, more preferably 1:1.0 to 1:1.8, likewise preferred, however, are also 1:0.4 to 1:1.8, 1:0.4 to 1:1.6, preferably 1:0.4 to 1:1.5; alternatively, on addition of more water, of 1:0.4 to 1:0.9, more particularly of 1:0.4 to 1:0.8, likewise preferably 1:0.4 to 1:0.7, with the proviso that the olefinically functionalized siloxane oligomer is derived from alkoxysilanes of the general formula II and III,
(ii) the ratio of the silicon atoms, selected from olefinically functionalized silicon atoms and from silicon atoms functionalized with a saturated hydrocarbon, to alkoxy groups in the silane oligomer or optionally in the general formula I is from 1:0.9 to 1:2.5, more particularly from 1:0.9 to 1:1.5, more particularly from 1:1.0 to 1:1.4; alternatively, on addition of more water, from 1:1.0 to 1:1.3, preferably from 1:1.0 to 1:1.2, with the proviso that the olefinically functionalized siloxane oligomer derives from alkoxysilanes of the general formula II and IV and of the formula III.

According to one alternative, compositions of purely olefinically substituted siloxane oligomers are prepared, more particularly of the formula I with a being an integer greater than or equal to 2; preferably, for at least 20 wt % of the siloxane oligomers, a is greater than or equal to 4, optionally greater than or equal to 8. Preferred olefinic groups are linear, branched or cyclic, alkenyl-, cycloalkenyl-alkylene-functional groups having in each case 2 to 16 C atoms, more particularly having 2 to 8 C atoms, preferably a vinyl, allyl, butenyl, such as 3-butenyl, pentenyl, hexenyl, ethylhexenyl, heptenyl, octenyl, cyclohexenyl-C1 to C8-alkylene, preferably cyclohexenyl-2-ethylene, such as 3'-cyclohexenyl-2-ethylene and/or cyclohexadienyl-C1 to C8-alkylene, preferably cyclohexadienyl-2-ethylene group. Particularly preferred is vinyl. The composition may optionally be based on a siloxane oligomer which has been prepared in the presence of tetraalkoxysilane.

Corresponding to a second preferred alternative, compositions of olefinically substituted and alkyl-substituted siloxane oligomers are prepared, more particularly of the formula I with a being greater than or equal to 1 and b being greater than or equal to 1, and in particular, for at least 20 wt % of the siloxane oligomers, especially of the formula I, (a+b) are an integer greater than or equal to 4, optionally greater than or equal to 8. In the case of these compositions it is further preferred if the molar ratio of A radicals to B radicals is 1:0 to 1:8, the ratio of a:b being more particularly 1:0 to 1:8, more particularly 1:0 or 1:1 to 1:8. The composition may optionally be based on a siloxane oligomer which has been prepared in the presence of tetraalkoxysilane.

Corresponding to a further preferred alternative, compositions of vinyl- and alkyl-substituted siloxane oligomers are prepared, more particularly of the formula I with a being greater than or equal to 1 and b being greater than or equal to 1, and more particularly, for 20 wt % of the siloxanes, (a+b) is an integer greater than or equal to 4, optionally greater than or equal to 8, preferably with a molar ratio of A radicals to B radicals of 1:0 to 1:8, more particularly of a:b as 1:0 to 1:8, more particularly 1:0 or 1:1 to 1:8. The compositions may optionally be based on a siloxane oligomer which has been prepared in the presence of tetraalkoxysilane.

With further preference the composition comprises olefinically functionalized siloxane oligomers with structural elements which are obtainable and/or derived from at least one of the alkoxysilanes, from olefinically functionalized alkoxysilanes of the general formula II and optionally from alkyl-functionalized alkoxysilane of the formula III, and optionally from a tetraalkoxysilane of the general formula IV which is $Si(OR^3)_4$, with the amount of silicon atoms in monomeric alkoxysilanes being preferably below 1% to 0% and the amount of structural elements of the siloxane oligomers with T structures is greater than or equal to 1%, more particularly 1% to 10%, it being possible further for at least 20 wt % of the siloxane oligomers to have a degree of oligomerization of (a+b+c) of greater than or equal to 4, optionally greater than or equal to 8.

A structural element—a monomeric siloxane unit—refers consistently to the individual structural unit M, D, T or Q, i.e. the structural unit which derives from an alkoxy-substituted silane and which is formed by at least partial hydrolysis to optionally complete hydrolysis and at least partial condensation in a condensate. In accordance with the invention it is possible in particular for the siloxane oligomers with the following structural elements to form, such as, preferably: $(R^1O)[(R^1O)_{1-x}(R^2)_xSi(A)O]_aR^1$; $(R^1O)[(R^1O)_{1-x}(R^2)_xSi(A)O]_a$; $[(R^1O)_{1-x}(R^2)_xSi(A)O]_a$; $[(R^1O)_{1-x}(R^2)_xSi(A)O]_a$; $(R^2)_xSi(A)O]_aR^1$; $(R^3O)[Si(Y)_2O]_c$; $[Si(Y)_2O]_cR^3$, $(R^3O)[Si(Y)_2O]_cR^3$; $[Si(Y)_2O]_c$, $(R^3O)[Si(B)(R^4)_y(OR^3)_{1-y}O]_bR^3$; $[Si(B)(R^4)_y(OR^3)_{1-y}O]_bR^3$, $[Si(B)(R^4)_y(OR^3)_{1-y}O]_b$; $(R^3O)[Si(B)(R^4)_y(OR^3)_{1-y}O]_bR^3$, which may form catenary, cyclic and/or crosslinked structures, and in the presence of tetraalkoxysilanes or their hydrolysis and/or condensation products, it is also possible for three-dimensionally cross-linked structures to be formed. The structural elements with free valencies on the Si atom are satisfied covalently via —O—Si, and the free valencies on the O atom are satisfied with —Si-bridged bonds of other structural elements, alkyl or optionally hydrogen. These structural elements may take up a disordered or else statistical arrangement in the condensates, and this arrangement, as the skilled person is aware, may also be controlled by the sequence of the addition and by the conditions of hydrolysis and/or condensation. The general formula I does not reproduce the composition or structure that it actually present. It corresponds to one idealized possibility of representation.

The composition preferably comprises siloxane oligomers which form by statistical and/or unordered homo- or co-hydrolysis and/or homo- or co-condensation and/or block condensation of the stated structural elements, based on the alkoxysilanes of the formulae II, III and/or IV substituted in accordance with the invention by A or B radicals, and/or which form under the selected experimental conditions.

The substitution pattern of the structural elements also applies, correspondingly, for the catenary, cyclic, cross-linked and/or three-dimensionally crosslinked siloxane oligomers in the composition that are not represented in idealized form, with it being possible for the silyl groups in the siloxane oligomers to be substituted, independently, as follows: with Y corresponds to an $OR^3$ or, in crosslinked and/or three-dimensionally crosslinked structures, independently of one another, $OR^3$ or $O_{1/2}$— in a siloxane bond, with radicals A and/or B, as defined, $R^3$ in the siloxane oligomers corresponds essentially to an alkyl radical, as defined for $R^3$, and in crosslinked and/or three-dimensionally crosslinked structures siloxane bonds with $O_{1/2}$ may also be formed from the radicals $OR_3$, in each case independently of one another, and/or these radicals, independently of one another, may be present as $O_{1/2}$, and optionally, independently, with $R^2$ and/or $R^4$, and which, as defined, correspond to an alkyl radical having 1 to 15 C atoms, with —$OR^1$, where $R^1$ may likewise, as defined, be an alkyl radical having 1 to 4 C atoms.

The invention also provides a composition comprising olefinically functionalized siloxane oligomers, more particularly at least one siloxane oligomer according to the idealized formula I, comprising as further components at least one organic solvent, one organic polymer, water, salt, filler, additive, pigment or a mixture of at least two of the stated components. The components may be added during the preparation of the composition and at a later point in time to the composition.

A particular advantage of the composition of the invention is that by virtue of its preparation it has a very low chlorine content and hence in the case of processing in cable compounds leads to a considerable improvement in the fire prevention properties. It is therefore a key advantage of the composition that as a liquid-phase product, optionally after removal of the hydrolysis alcohol and any solvent added, it can be used directly in an economic way in accordance with the invention. A further advantage of the compositions of the invention is that as a result of the increased fraction of T structures, in combination with good processing properties in extruders, they lead to improved elongation at break on the part of the thermoplastics and elastomers processed therewith, and it has also been possible to improve the tensile properties.

Olefinically functionalized siloxane oligomer compositions of the invention have an alcohol content in relation to the composition, preferably a free alcohol content, of below 2 wt % to 0.0001 wt %, more particularly below 1.8 wt %, preferably below 1.5 wt %, more preferably below 1.0 wt %, very preferably below 0.5 wt % down to the detection limit. A composition has this low alcohol content, preferably free alcohol content, over at least 3 months, preferably over a period of 6 months. These low VOC contents may be ensured by the process of the invention, which provides particularly low-chlorine siloxanes with a low alkoxy content.

The invention provides a process for preparing a composition comprising olefinically functionalized siloxane oligomers, and also, in particular, compositions obtainable by this process, by reacting (at least)

(i) an olefinically functionalized alkoxysilane of the general formula II, $$A\text{-}Si(R^2)_x(OR^1)_{3-x} \qquad (II),$$

where A in formula II corresponds to an olefinic radical which is selected in particular from a linear, branched or cyclic alkenyl- or cycloalkenyl-alkylene-functional group having in each case 2 to 16 C atoms, $R^2$ independently corresponds to a linear, branched or cyclic alkyl radical having 1 to 15 C atoms and x is 0 or 1, and $R^1$ independently corresponds to a linear, branched and/or cyclic alkyl radical having 1 to 4 C atoms, (ii) in the presence of a hydrolysis and/or condensation catalyst, more particularly of HCl, saturated or unsaturated organic acids, such as formic acid or acetic acid, and/or fatty acids, such as myristic acid, and/or polybasic organic acids, such as citric acid, fumaric acid, (i.1) optionally with (at least) an alkoxysilane of the formula III, $$B\text{—}Si(R^4)_y(OR^3)_{3-y} \qquad (III),$$

where in formula III B corresponds to a saturated hydrocarbon radical selected in particular from a linear, branched or cyclic alkyl radical having 1 to 16 C atoms, $R^3$ corresponds independently at each occurrence to a linear, branched and/or cyclic alkyl radical having 1 to 4 C atoms, and $R^4$ corresponds to a linear, branched or cyclic alkyl radical having 1 to 15 C atoms, and y is 0 or 1, and (i.2) optionally with (at least) a tetraalkoxysilane of the formula IV, with $R^3$ in formula IV independently at each occurrence being a linear, branched and/or cyclic alkyl radical having 1 to 4 C atoms, $$Si(OR^3)_4 \qquad (IV),$$

and (iii) with a defined amount of water, more particularly of greater than or equal to 0.5 to 1.5 mol, more particularly of 0.70 to 1.5 mol, preferably of greater than or equal to 0.75 to 1.5 mol, more preferably of 1.0 to 1.5 mol, alternatively preferably 0.75 to 1.0 mol of water per mole of silicon atoms in the alkoxysilanes used, optionally in the presence of a solvent, preferably alcohol, more particularly in the presence of 0.001 to 5.0 volume units of alcohol per volume unit of alkoxysilane, to give the siloxane oligomers, more particularly with x=0 and y=0, and (iv) substantially removing the hydrolysis alcohol and the solvent optionally present, and (v) at least once during step (iv) or subsequently adding in each case a defined further amount of alcohol and carrying out removal, preferably by distillation, more particularly with addition of 0.001 to 5.0 volume units of alcohol per volume unit of alkoxysilane, and in particular a composition comprising a siloxane oligomer or siloxane oligomers is prepared, (vi) more particularly with a chlorine content, more particularly total chloride content, in the composition of less than or equal to 100 mg/kg to 0 mg/kg, more particularly less than or equal to 70 mg/kg, preferably less than or equal to 50 mg/kg, the hydrolysable chloride content being, with further preference, less than or equal to 20 mg/kg to 0 mg/kg, preferably less than or equal to 10 mg/kg, more preferably less than or equal to 5 mg/kg, and (vii) a weight-average molecular weight (Mw) of greater than 410 g/mol is obtained, the weight-average molecular weight (Mw) being more particularly greater than or equal to 410 g/mol and the number-average molecular weight (Mn) being greater than or equal to 370 g/mol, with the polydispersity, as the ratio of Mw/Mn, being 1.00 to 1.25, and optionally (ix) greater than or equal to 1% of the silicon atoms in the olefinically functionalized siloxane oligomer are present, in relation to the sum total of silicon atoms in the siloxane oligomer, as T structure, preferably greater than or equal to 3% to less than 10%, more preferably greater than or equal to 4 to 10.

In accordance with the invention the composition comprising olefinically functionalized siloxane oligomers, in particular in step (v) after the removal of the alcohol or after the end of step (v), more particularly subsequent to step (v), is obtained as a liquid-phase product.

According to one particularly preferred embodiment, an alcohol is used as solvent that is preferably selected from methanol, ethanol or a mixture comprising one or both alcohols.

In accordance with the process of the invention it is particularly preferred if in step (iii) reaction takes place with a defined amount of water in the presence of an alcohol in an amount of 0.001 to 5.0 volume units of alcohol per volume unit of alkoxysilane, and/or in step (v), at least once during step (iv) or subsequently, a further defined amount of alcohol is added and removal is carried out, more particularly the alcohol being removed by distillation. Alcohol can be added in the stated amounts preferably 1 to 6 times, preferably 2 to 6 times. The alcohol corresponds preferably to the hydrolysis alcohol formed.

By way of the frequency of addition and/or the amount added of solvent, preferably alcohol, it is possible, together with the amount of water, to optimize the molecular weight and the molecular weight distribution and in this way largely to avoid any formation of high molecular mass oligomers. The unwanted oligomers of relatively high molecular mass are formed only at a low level.

Preferably in (vii), in step (v) after the removal of the alcohol or subsequent to step (v), a composition is obtained with olefinically functionalized siloxane oligomers whose molecular weight Mw is greater than or equal to 250 to 750 g/mol, in relation to the overall composition, to an extent of greater than or equal to 85% (area %, GPC).

It is further preferred if in particular in (vii), in step (v) after the removal of the alcohol, or subsequent to step (v), a composition is obtained with olefinically functionalized siloxane oligomers whose molecular weight Mw is greater than or equal to 250 to 1000 g/mol, in relation to the overall composition, to an extent of greater than or equal to 95% (area %, GPC).

According to one particularly preferred process variant, reaction takes place in step (iii) with a defined amount of water in the presence of an alcohol in an amount of 0.05 to 2.5 volume units of alcohol per volume unit of alkoxysilane, more particularly with 0.1 to 2.0 volume units of alcohol per volume unit of alkoxysilane, preferably 0.2 to 1.5, more preferably 0.2 to 1.0 or 0.2 to 0.9. Preferably 0.5 plus/minus 0.4 volume units of alcohol per volume unit of alkoxysilane.

In the case of a reaction of VTMO or VTEO, preferably, for the purpose of dilution plus metering, 0.5 to 2.5 or 0.5 to 2.0 and/or in step (v) at least once during step (iv) or thereafter a defined further amount of alcohol is added and removal takes place. For the further addition in (v), (iv) or subsequently, it is likewise possible, two or more times, for 0.001 to 5 volume units, more particularly 0.1 to 2.5 volume units, of alcohol to be added per volume unit of alkoxysilane. These measures may be repeated as desired, preferably 1 to 10 times. The alcohol removed by prior distillation and the alcohol purified may be used again.

According to the process of the invention, it is possible in a simple and economical way to prepare a composition comprising olefinically functionalized siloxane oligomers in which greater than or equal to 1% of the silicon atoms in the olefinically functionalized siloxane oligomer, in relation to the sum total of silicon atoms in the siloxane oligomer, are obtained as T structure, more particularly 0.5 to 10, preferably 1.0 to 10.0%.

Likewise in accordance with the process of the invention it is possible, in a simple and economical way, to prepare a composition comprising olefinically functionalized siloxane oligomers in which the amount of silicon atoms in monomeric alkoxysilanes, more particularly of the formula II, III and/or IV, or the hydrolysis products thereof is less than or equal to 3%, more particularly down to the detection limit or to 0%, in relation to all the silicon atoms, preferably less than or equal to 2%, more preferably less than or equal to 1%, very preferably less than or equal to 0.5%.

It is particularly preferred, according to the process of the invention, if reaction takes place in step (v) with a defined amount of water in the presence of an alcohol in an amount of 0.001 to 5.0 volume units of alcohol per volume unit of alkoxysilane, and/or, in step (vii) at least once during step vi or subsequently, a further defined amount of alcohol is added, and removal takes place, the alcohol more particularly being removed by distillation. Alcohol may be added in the stated amounts preferably 1 to 6 times, preferably 2 to 6 times. The alcohol corresponds preferably to the hydrolysis alcohol formed.

The ratio of the alcohol in step (iii) to step (v) is preferably a ratio of 1:5 to 5:1, more preferably of 1:2 to 2:1, more preferably 1:1. It is further preferred in the process of the invention if at least once during step vi or thereafter a defined amount of alcohol of 0.0001 to 5.0 volume units of alcohol per volume unit of alkoxysilane is metered in and subsequently removal takes place, the alcohol in particular being removed by distillation. Distillation for this purpose takes place under reduced pressure and at elevated temperature, more particularly under a pressure of less than 300 mbar, preferably less than 180 mbar, more preferably less than 120 mbar, with the pressure being preferably set such that the temperature load on the liquid-phase product is around 90° C. or a lower temperature, more particularly from 0 to 90° C., preferably 20 to 90° C.

In the sense of step (v) of the process of the invention it is also possible with preference to add, or add further, more than once, a defined amount of alcohol, preferably 2 to 5 times, more particularly 2, 3 or 4 times. The metered addition may take place in each case in a portion or in each case continuously, and a respectively continuous metered addition may take place advantageously over 1 minute up to one hour. Furthermore, the addition or further addition of the alcohol takes place preferably below the liquid level of the reaction product in the liquid phase. The liquid phase here may additionally be mixed, by means of stirring, for example. The volume of alcohol added additionally is preferably approximately the same as that used beforehand during the reaction in step (iii). It is possible advantageously to use 0.001 to 5 volume units of alcohol to each volume unit of trialkoxysilane.

In the process of the invention it is preferred if the alkoxysilanes of the formulae II, III and/or IV are subjected to at least partial hydrolysis and condensation in the presence of an acidic catalyst, in particular with hydrogen chloride, and preferably the alcohol, more particularly encompassing the alcohol used in step v, the hydrolysis alcohol and also the added alcohol from step vii, is substantially completely removed.

According to one preferred embodiment, an alkenyl-functionalized alkoxysilane of the general formula II is reacted optionally together with an alkylalkoxysilane of the general formula III in the presence of a condensation catalyst. With further preference an alkenyltrialkoxysilane and optionally an alkyltrialkoxysilane are reacted in each case. The reaction may take place optionally in the presence of a solvent, preference being given to using the corresponding alcohol of the alkoxysilane. With particular advantage it is possible in the process of the invention to use 0.001 to 5 volume units of the corresponding alcohol per volume unit of alkoxysilane, more particularly trialkoxysilane. With further preference from 0.1 to 4, more particularly 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.5, 3, 3.5 volume units are used per volume unit of trialkoxysilane.

The solvent used and/or the alcohol used are anhydrous; more particularly, the solvent or the alcohol is used with a water content of less than or equal to 1 ppm by weight. In the case of solvents containing water, this water content must be taken into account in the reaction.

The olefinically functionalized alkoxysilane used is preferably a silane of the general formula II,

$$A\text{-}Si(R^2)_x(OR)_{3-x} \quad (II)$$

where A is selected from a linear, branched or cyclic alkenyl- or cycloalkenyl-alkylene-functional group having in each case 2 to 18 C atoms, more particularly having 2 to 16 C atoms, preferably having 2 to 8 C atoms, more preferably an alkenyl group having one to two double bonds, preferably a vinyl, allyl, butenyl, pentenyl, hexenyl, ethylhexenyl, heptenyl, octenyl, cyclohexenyl-C1 to C8-alkylene, preferably cyclohexenyl-2-ethylene, such as 3'-cyclohexenyl-2-ethylene, and/or cyclohexadienyl-C1 to C8-alkylene, more preferably a cyclohexadienyl-2-ethylene group, A being more preferably vinyl, x in particular being 0, and $R^1$ independently being a linear, branched and/or cyclic alkyl radical having 1 to 4 C atoms, more particularly a methyl, ethyl or propyl group.

Used preferably as alkoxysilane of the formula III is an alkoxysilane with an unsubstituted hydrocarbon radical B,

$$B\text{—}Si(R^4)_y(OR^3)_{3-y} \quad (III)$$

where the group B is selected from a methyl, ethyl, propyl, butyl, isobutyl, n-butyl, tert-butyl, pentyl, n-pentyl, isopentyl, neopentyl, hexyl, isohexyl, neohexyl, 2,2-dimethylbutyl, 2,3-dimethylbutyl, 2-methylpentyl, 3-methylpentyl, octyl, n-octyl, isooctyl, nonyl, decyl, undecyl, dodecyl, $C_{13}H_{27}$, $C_{14}H_{29}$, $C_{15}H_{31}$ and hexadecyl group and $R^3$ is a methyl, ethyl or propyl group and y is 0 or 1.

And $R^2$ and $R^4$ may be independently of one another, in formula II and III, preferably methyl, ethyl, propyl, butyl, pentyl, hexyl, cyclohexyl, heptyl, octyl, nonyl and also further alkyl groups known to the skilled person, including the structural isomers. According to one alternative preferred embodiment, unsubstituted hydrocarbons having branched and/or cyclic alkyl radicals with 3 to 16 C atoms are employed as radical B. According to another preferred alternative of the invention, linear alkyl radicals having 1 to 7 C atoms are used as unsubstituted hydrocarbon radical B.

There is at least partial hydrolysis, and in particular at least partial co-condensation; preferably, the condensable, partially hydrolysed alkoxysilanes are subjected to substantially complete condensation. With particular preference, partial hydrolysis and condensation takes place only to the extent desired for the preparation of the oligomers with a preferred degree of oligomerization.

In accordance with the invention the hydrolysis alcohol is removed completely, preferably by distillation, and the composition according to the invention is obtained. Particularly gentle distillation of the hydrolysis alcohol and/or the solvent takes place under reduced pressure. Depending on procedure, a particularly economic process can be carried out without the addition of a solvent. In accordance with the invention, the composition prepared in this way, following removal of the hydrolysis alcohol and any solvent, does not itself have to be purified further, and more particularly does not itself have to be distilled, in order to be suitable for the uses according to the invention. Depending on preparation procedure, the composition may optionally be filtered or decanted following removal of the hydrolysis alcohol. The process of the invention is therefore very much more economic than known processes where the oligomer, in order to be suitable for further application, must be purified by distillation.

Again preferably in the process it is possible to use at least one olefinically functionalized alkoxysilane of the general formula II that is selected from vinyltriethoxysilane, vinyltrimethoxysilane, and, optionally, from alkoxysilanes of the formula III, the alkoxysilanes of the formula III being selected from methyltriethoxysilane, methyltrimethoxysilane, ethyltriethoxysilane, ethyltrimethoxysilane, propyltriethoxysilane, propyltrimethoxysilane, butyltriethoxysilane, butyltrimethoxysilane, n-butyltriethoxysilane, n-butyltrimethoxysilane, isobutyltriethoxysilane, isobutyltrimethoxysilane, hexyltriethoxysilane, hexyltrimethoxysilane, n-hexyltriethoxysilane, n-hexyltrimethoxysilane, isohexyltriethoxysilane, isohexyltrimethoxysilane, octyltriethoxysilane, octyltrimethoxysilane, n-octyltriethoxysilane, n-octyltrimethoxysilane, isooctyltriethoxysilane, isooctyltrimethoxysilane, undecyltriethoxysilane, undecyltrimethoxysilane, decyltriethoxysilane, decyltrimethoxysilane, nonadecyltriethoxysilane, nonadecyltrimethoxysilane, dodecyltriethoxysilane, dodecyltrimethoxysilane, $C_{13}H_{27}$-triethoxysilane, $C_{13}H_{27}$-trimethoxysilane, $C_{14}H_{29}$-triethoxysilane, $C_{14}H_{29}$-trimethoxysilane, $C_{15}H_{31}$-trimethoxysilane, $C_{15}H_{31}$-triethoxysilane, hexadecyltriethoxysilane and hexadecyltrimethoxysilane, dimethyldimethoxysilane (DMDMO), dimethyldiethoxysilane, propylmethyldimethoxysilane, propylmethyldiethoxysilane, n-octylmethyldimethoxysilane, n-hexylmethyldimethoxysilane, n-hexylmethyldiethoxysilane, propylmethyldimethoxysilane, propylmethyldiethoxysilane, cyclohexyltriethoxysilane, n-propyltri-n-butoxysilane, hexadecylmethyldimethoxysilane and/or hexadecylmethyldiethoxysilane, and also mixtures of these silanes, or a mixture comprising at least two of the silanes, and also the transesterification products thereof.

According to the process of the invention, a composition comprising siloxane oligomers is obtained, preferably as liquid-phase product, more preferably after implementation of step (v), that straight after implementation of steps i, iii, iv and v and also, optionally, of steps i.1 and/or i.2 has the preferred inventive low chlorine content, more particularly total chloride content, of less than or equal to 100 mg/kg to 0 mg/kg, more particularly less than or equal to 75 mg/kg, preferably less than or equal to 50 mg/kg, the hydrolysable chloride content being preferably less than 5 mg/kg to 0 mg/kg, preferably less than or equal to 4 mg/kg, and for which preferably greater than or equal to 3% of the silicon atoms in the olefinically functionalized siloxane oligomer, in relation to the sum total of silicon atoms in the siloxane oligomer, are present as T structure.

The reaction takes place preferably in the presence of a defined amount of water of greater than 0.60 to 1.48 mol of water per mole of silicon atoms in the alkoxysilanes of the formula II and/or III and optionally of the formula IV that are used, more particularly 0.70 to 1.45 mol of water, preferably greater than 0.75 to 1.43 mol of water, more preferably greater than or equal to 1.2 to 1.43 mol of water, preferably from 1.25 to 1.4 mol of water per mole of silicon atoms in the alkoxysilanes of the formula II and/or III and also, optionally, of the formula IV that are used. Considered to be likewise disclosed are all numerical values for mol of water that are included within the disclosed range, in particular down to the second decimal place, such as 0.61; 0.62; 0.63; 0.64; 0.65; 0.66; 0.67; 0.68; 0.69; 0.70 to 1.05 and all in-between numerical values 1.06; 1.07; 1.08; 1.09; 1.11; 1.12; 1.13; 1.14; 1.15; 1.16; 1.17; 1.18; 1.19; 1;21; 1.22; 1.23; 1.24; 1.26; 1.27; 1.28; 1.29; 1.30; 1.31; 1.32; 1.33; 1.34; 1.35; 1.36; 1.37; 1.38; 1.39; 1.40; 1.41; 1.42; 1.43; 1.44; 1.45; 1.46; 1.47. The water is preferably fully demineralized. To the skilled person it is clear that the water may be introduced initially, added in portions, added continuously or added together with one or all the silanes to the process. The water is preferably added continuously or with at least one interruption over a period of less than 1 minute to 100 minutes, and the reaction of the alkoxysilanes is preferably carried out at reaction temperatures in the range of preferably 40° C. to 80° C., more preferably in the range from 50° C. to 80° C., more particularly at a pH of less than 7.

Generally speaking, the water or a quantity of water, in accordance with Section v of the process a) may be metered in continuously or at least with an interruption over a period of 1 to 1000 minutes with a temperature in the reaction mixture of 5 to 90° C. being set, more particularly 37 to 90° C., preferably 40 to 90° C., more preferably from 50 to 90° C., with further preference 50 to 80° C., the pH preferably being below 7; optionally the water is added together with the catalyst and optionally with a solvent, more particularly with an alcohol. The reaction may in that case preferably take place such that b) the mixture from a) (reaction mixture) is treated or reacted further optionally for at least 10 minutes to 36 hours, more particularly from 10 minutes to 8 hours (h), preferably at 5 to 80° C., more preferably at 40 to 80° C., preferably with mixing, and the reaction mixture may optionally also continue reacting as it cools. To adjust the molecular weight, an alkoxytrialkylsilane, more particularly alkoxytrimethylsilane, can be added to the process. The composition obtained in this way can then be decanted or heated for distillative removal of the alcohol, such as the hydrolysis alcohol. From this crude product, the alcohol, optionally including catalyst, more particularly HCl, is preferably removed by distillation with heating under reduced pressure.

According to one preferred embodiment, in the process according to Section vi, the hydrolysis alcohol and the solvent optionally present, more particularly the added alcohol, are removed by distillation and preferably (15.i, cf. Claim 15) at least once, preferably two to six times, during the distillative work-up, more particularly in step iv or v, or subsequently, a defined amount of alcohol is added—in particular, per volume unit of alkoxysilane, 0.001 to 5.0 volume units of alcohol are metered in; and/or (15.ii, cf. Claim 15) before or during the distillative removal of the hydrolysis alcohol, in particular in step iv or v, and optionally of solvent, a defined amount of a reducing agent is added, such as alkali metal, alkaline earth metal, aluminium, a metal hydride, or a defined amount of a base, such as preferably HMDS, an amine or an alkali metal alkoxide, and thereafter in particular the olefinically functionalized siloxane oligomer, present as the liquid-phase product, is filtered or decanted; alternatively or additionally, contacting with an ion exchanger is performed. As a result of the filtration and/or decanting, precipitates or flocs that have formed can be removed substantially from the composition comprising the siloxane oligomer. Preference is given to using a defined amount of a reducing agent, especially an inorganic reducing agent, more preferably a metallic reducing agent, such as alkali metal, preferably sodium, or alkaline earth metal, preferably magnesium or calcium, or aluminium, and as metal hydride, preferably Li aluminium hydride, aluminium hydride, or, as base, preferably gaseous ammonia, LDA (Li diisopropylamide), Li isopropylhexylamide, potassium hexamethylsilazane, hexamethyldisilazane, an alkali metal alkoxide, more particularly Na or K methoxide or Na or K ethoxide, or alkali metal alkylate, such as butyl-Li. Additionally used in the process may also be metal hydrides known to the skilled person, such as NaH, or else lithium aluminium hydride or bases which form sparingly soluble precipitates with the hydrogen chloride, in order to achieve a further lowering of the chlorine/chloride content of the composition. Bases suitable for the process ought not to form water on reaction with the catalyst, such as HCl, or with organically bonded chlorine, such as Cl—Si.

In all variants of the process according to the invention, the alcohol that is already present and/or the alcohol formed during the reaction is removed substantially, preferably completely, from the reaction mixture, to give a free alcohol content of preferably not more than 1.0 wt %, more particularly below 0.8% to 0.0001 wt %. The distillative removal of the alcohol is carried out preferably under reduced pressure. The distillative removal of the alcohol is preferably continued until the column overhead temperature is reached that corresponds to the boiling point of water, or preferably until a reduced pressure of 100 mbar, more particularly less than or equal to 100 mbar and greater than or equal to 0.01 mbar, can be durably set. Generally speaking, the resulting composition of the invention is then substantially solvent-free, more particularly alcohol-free. The composition obtained accordingly preferably corresponds directly to the composition of the invention, and preferably need not itself be further purified.

Before or else after the removal of the alcohol, the composition may be admixed with at least one processing assistant such as silicone oil, such as polydimethylsiloxane, paraffin, liquid paraffin, or a mixture comprising one of these processing assistants.

According to one preferred variant of the process, the alkoxysilanes of the general formulae II, III and/or IV are subjected to at least partial hydrolysis and condensation in the presence of an acidic catalyst, more particularly with hydrogen chloride. Where necessary the hydrolysis and condensation may also take place in the presence of HCl and a co-catalyst. Co-catalysts contemplated include fatty acids. Alternatively it is possible to use HCl and saturated or unsaturated organic acids as well, such as formic acid or acetic acid, and/or fatty acids, as for example myristic acid, and/or polybasic organic acids, such as citric acid, fumaric acid, as catalyst or as co-catalyst with HCl.

It is further preferred, in accordance with the process, to use the silane of the formula II and the silane of the formula III in a ratio of 1:0 to 1:8 and/or to use the silane of the formula II in a ratio to the silane of the formula IV in a ratio of 1:0 to 1:0.22, preferably 1:0 to 1:0.20, more particularly of 1:0 to 1:0.15, preferably 1:0 to 1:0.10, more preferably 1:0 to 1:0.05, the silane of the formula II and the silane of the formula III being used preferably in a ratio of about 1:0 or approximately in the ratio 1:1 or in the ratio of 1:0 to 1:2, preferably 1:0 to 1:1. Alternatively preferred is also a process in which the silane of the formula II and the silane of the formula III are used in a ratio of 1:0 to 1:2, preferably of 1:1, and/or to use the silane of the formula II in relation to the silane of the formula IV in a ratio of 1:0 to 1:0.20, preferably 1:0 to 1:0.10, more preferably 1:0 to 1:0.5, preferably in a ratio of 1:0.10 to 1:0.05 or of 1:0.1. The siloxane oligomers produced in the stated ratios exhibit properties which are particularly homogeneous in performance terms; the silane of the formula IV is used preferably for greater crosslinking in the oligomer or else of the oligomer with a substrate.

With particular preference, in accordance with one alternative, the silane of the formula II and the silane of the formula III are used approximately in a ratio of 1:1; according to another preferred alternative, the silane of the formula II and the silane of the formula IV are used in a ratio of approximately 1:0.1, and additionally with preference the silane of the formula II and the silane of the formula III are present in a ratio of approximately 1:1.

Preferred alcohols correspond to the hydrolysis alcohol formed by the at least partial hydrolysis and/or condensation. They include ethanol or methanol. To the skilled person it is clear that the reaction can also be carried out in the presence of another customary solvent, preference being given to those which can be distilled off easily and preferably completely—these may be, for example but not conclusively, ethers, ketones, hydrocarbons or esters. Useful solvents may alternatively be ethyl acetate, THF, ketones, ethers or hydrocarbons. To the skilled person it is clear that for reasons of business and economy an alcohol is used as solvent that is also formed as hydrolysis alcohol. Mixtures of alcohols may therefore also be used in principle. In all process variants, the solvent and the alcohol formed in the reaction are preferably removed by distillation from the reaction mixture.

According to a further preferred process variant, the degree of oligomerization of at least 20 wt % for the siloxane oligomers with n being the number of silicon atoms is set such that for these oligomers n is greater than or equal to 8. With further preference, according to the process of the invention, in particular more than 1% of the olefinically functionalized silicon atoms are obtained as T structure; preferably this may also be more than 2%, more preferably greater than or equal to 3%, very preferably greater than or equal to 4% or else greater than or equal to 5% and also greater than or equal to 7.5% to 10%; additionally or alternatively, with preference, more than 0.3% of the silicon atoms in the siloxane oligomer that are functionalized with a saturated hydrocarbon are also present as T structure, more particularly 0.3% to 2%.

In the process of the invention, preferably, the dynamic viscosity of the composition is set at less than or equal to 1000 mPa s, preferably to less than or equal to 740 mPa s, more preferably to less than or equal to 500 mPa s to greater than or equal to 1 mPa s.

Further it is possible in the process for the composition, more particularly the liquid-phase product, preferably after the distillative removal of the solvent and/or alcohol, to be contacted with an ion exchanger, more particularly an anion exchanger, preferably an amine-functional ion exchanger, in order further to reduce the chloride content. In this process step it is advantageous that this measure, in contrast to a distillation, does not alter the degree of oligomerization and/or the degree of branching of the product. In the case of a distillation there would automatically be a separation of the siloxane oligomer into low, medium and high boilers (liquid phase). Through the use of the ion exchanger in accordance with the invention, the degree of oligomerization of the siloxane oligomers remains the same, and the chloride content can be lowered further. In the process of the invention it is also possible for the contacting with the ion exchanger to be combined with one of the measures by addition of a defined amount of alkali metal, alkaline earth metal, aluminium, a metal hydride or a base.

By contacting with an ion exchanger it is possible with preference for the chloride content or the chlorine content in weight-ppm of the olefinic siloxane oligomers to be reduced by at least 80% in relation to the siloxane oligomers supplied to the ion exchanger. With further preference the chlorine content in weight-ppm of the olefinic siloxane oligomers in relation to those supplied is reduced by at least 85%, preferably by at least 90%, more preferably at least by 92%, likewise preferably at least by 95%, and more preferably by at least 98%. Depending on olefinically functionalized siloxane oligomer, and depending on the initial concentration of chlorine, the flow rate and the contact time with the anion exchanger, the chlorine content can be lowered preferably to less than or equal to 100 mg/kg, preferably to less than or equal to 50 mg/kg, more preferably to less than or equal to 25 mg/kg.

In the case of olefinically functionalized siloxane oligomers with a chlorine content, i.e. with hydrolysable chlorine, more particularly chlorine-functional alkylalkoxysilanes and/or alkylalkoxysilanes with HCl, the hydrolysable chloride content may be reduced, preferably at flow rates of 0.01 m/h to 15 m/h, preferably up to 5 m/h, more particularly at up to 2.5 m/h, by at least 80%, more particularly by at least 85%, preferably by at least 90%, more preferably at least by 92%, likewise preferably at least by 95%, and more preferably by at least 98%; in this case, in particular, the olefinically functionalized siloxane oligomers are not subjected to further condensation, and the anion exchanger column preferably has a diameter of 3 cm and a height of 15 cm. Very good results in diminishing hydrolysable chlorine, of up to 80%, are also obtained at flow rates of up to 10 m/h.

In the process of the invention, the anion exchanger has a carrier polymer with quaternary alkylammonium groups and/or with tertiary dialkylamino groups, the quaternary alkylammonium groups in particular having essentially hydroxide ions as counterions, and/or the tertiary dialkylamino groups being present in the form of the free base. It is particularly preferred in this context if the basic anion exchanger is a styrene-divinylbenzene copolymer having trialkylammonium groups, more particularly in the OH form, and/or a styrene-divinylbenzene copolymer having dialkylamino groups in the form of the free base. When using basic anion exchangers with a styrene-divinylbenzene copolymer having trialkylammonium groups in the chloride form, the chlorides are converted into the OH form prior to use, using an alkali metal hydroxide solution, for example. Alkali metal hydroxide solutions used are preferably aqueous solutions of potassium hydroxide, sodium hydroxide or else other water-soluble or water/alcohol-soluble bases such as ammonia or alkali metal carbonates such as $Na_2CO_3$. After the conversion of the anion exchanger into the OH form, before the contacting with the olefinic siloxane oligomers, the anion exchanger is rinsed with an alcohol, in order in particular to displace excess water. The alcohol used is preferably the alcohol that would be formed by hydrolysis of the respective alkoxy groups. In the case of methoxy groups, methanol, or ethanol in the case of ethoxy groups in the alkoxysilane.

Quaternary ammonium groups include not only alkylammonium but also N-alkyl-imine-functional groups, such as N-alkylpyridinium groups. Suitable alkyl groups contain 1 to 20 C atoms, preferably with 1 to 4 C atoms, and are preferably methyl or ethyl groups. In accordance with the invention the weakly basic anion exchangers are loaded with hydroxide ions and in particular they have nitrogen-containing groups.

In accordance with the invention it is further preferred if the alkoxysilanes of the formulae II, III and/or IV are subjected to at least partial hydrolysis and condensation in the presence of the defined amount of water and of a hydrolysis and condensation catalyst, such as a mineral acid, such as HCl, an organic saturated or unsaturated carboxylic acid, such as formic acid, and/or fatty acid, for example, and the alcohol preferably, more particularly both the hydrolysis alcohol and any added alcohol, is removed. The hydrolysis alcohol and/or the added alcohol correspond to the free alcohol. With particular preference the amount of free alcohol in the overall composition is less than or equal to 2 wt % to 0.001 wt %, more particularly less than 2 wt % to 0.01 wt %, more preferably less than or equal to 1 wt % to 0.01 wt % down to the detection limit.

It has surprisingly emerged that the functional siloxane oligomers obtained by the process of the invention, in view of the further reduction in the chlorine content, are significantly more stable with respect to a hydrolysis, despite the fact that, in contrast to hitherto, they are no longer distilled at cost and inconvenience. As a result, the siloxane oligomers of the invention prove to be more stable than known oligomers and at the same time their monomeric alkoxysilane content is reduced relative to that of the oligomeric liquid-phase products of the prior art.

The solvents content, such as VOC content, more particularly free alcohol content, that is stable over a period of 3 to 6 months, in relation to the overall composition, is preferably below 2 wt %, more particularly less than or equal to 1 wt %, very preferably less than or equal to 0.4 wt %, preferably less than or equal to 0.3 wt %.

Compounds of the formula II that can be used in accordance with the invention are as follows: vinyltriethoxysilane, vinyltrimethoxysilane, allyltriethoxysilane, allyltrimethoxysilane, butenyltriethoxysilane, butenyltrimethoxysilane, cyclohexenyl-alkylene-trimethoxysilane, more particularly cyclohexenyl-2-ethylene-trimethoxysilane, cyclohexenyl-2-ethylene-triethoxysilane, more preferably 3'-cyclohexenyl-2-ethylene-triethoxysilane and/or 3'-cyclohexenyl-2-ethylene-trimethoxysilane, cyclohexenedienyl-alklylenetriethoxysilane, hexenyltriethoxysilane, hexenyltrimethoxysilane, ethylhexenyltrimethoxysilane, ethylhexenyltriethoxysilane, octenyltriethoxysilane, octenyltrimethoxysilane, particular preference being given to the methoxy-substituted compounds. It is likewise possible to use alkoxysilanes with mixed functionally, with ethoxy and methoxy groups.

Alkylalkoxysilane compounds of the formula III that can be used with preference are as follows:

Compounds of the formula III with y=0 or 1, where B corresponds to a linear or branched alkyl radical having 1 to 18 C atoms, more particularly having 1 to 8 C atoms, preferably to a methyl, ethyl, more preferably n-propyl, isopropyl, butyl, pentyl, hexyl, heptyl, octyl, hexadecyl or octadecyl radical, $R^4$ corresponds to a linear, branched or cyclic alkyl radical having 1 to 15 C atoms, more particularly having 1 to 8 C atoms, preferably to a methyl, ethyl, more preferably n-propyl, isopropyl and/or octyl radical, and $R^3$ corresponds to a linear and/or branched alkyl radical having 1 to 3 C atoms, more preferably to a methyl, ethyl and/or isopropyl or n-propyl radical. More preferably B is a methyl, ethyl, propyl, octyl, hexadecyl or octadecyl radical and $R^4$ is a methyl or ethyl radical and $R^1$ is a methyl or ethyl radical, particular preference being given to those which are methoxy-substituted.

Also preferably the unsubstituted hydrocarbon radical B independently in formulae I and/or III may correspond to a linear, branched or cyclic alkyl radical having 1 to 16 C atoms, more particularly a methyl, ethyl, propyl, n-propyl, isopropyl, butyl, n-butyl, isobutyl, n-octyl, isooctyl, octyl, or hexadecyl group. Also preferably the radical B may independently be selected from tert-butyl, pentyl, n-pentyl, isopentyl, neopentyl, hexyl, isohexyl, neohexyl, heptyl, 2,2-dimethylbutyl, 2,3-dimethylbutyl, 2-methylpentyl, 3-methylpentyl, neooctyl, nonyl, decyl, undecyl, dodecyl, 2-methylheptyl, 3-methylheptyl, 4-methylheptyl, 2,2-dimethylhexyl, 2,3-dimethylhexyl, 2,4-dimethylhexyl, 2,5-dimethylhexyl, 3,3-dimethylhexyl, 3,4-dimethylhexyl, 3-ethylhexyl, 2,2,3-trimethylpentyl, 2,2,4-trimethylpentyl, 2,3,3-trimethylpentyl, 2,3,4-trimethylpentyl, 3-ethyl-2-methylpentyl, 3-ethyl-3-methylpentyl, 2,2,3,3-tetramethylbutyl, $C_{13}H_{27}$, $C_{14}H_{29}$ and a $C_{15}H_{31}$ group. According to one alternative, the alkyl radical may be branched or cyclic with 3 to 16 C atoms, or linear with 2 to 7 C atoms.

It is particularly preferred if in formulae I and/or II, the olefinic radical A is a vinyl group, and independently thereof, in formulae I and/or III, the unsubstituted hydrocarbon radical B is selected from a methyl, ethyl, propyl, butyl, isobutyl, n-butyl, tert-butyl, pentyl, n-pentyl, isopentyl, neopentyl, hexyl, isohexyl, neohexyl, 2,2-dimethylbutyl, 2,3-dimethylbutyl, 2-methylpentyl, 3-methylpentyl, heptyl, octyl, n-octyl, isooctyl, nonyl, decyl, undecyl, dodecyl, $C_{13}H_{27}$, $C_{14}H_{29}$, $C_{15}H_{31}$ and hexadecyl group, and independently at each occurrence $R^1$ is a methyl, ethyl or propyl group and $R^3$ independently is a methyl, ethyl or propyl group.

Preferred compounds of the formula III, stated by way of example, are as follows: methyltrimethoxysilane, methyltriethoxysilane (MTES), propyltrimethoxysilane (PTMO), dimethyldimethoxysilane (DMDMO), dimethyldiethoxysilane, propylmethyldimethoxysilane, propylmethyldiethoxysilane, n-propyltrimethoxysilane, n-propyltriethoxysilane, isopropyltrimethoxysilane, isopropyltriethoxysilane, n-octylmethyldimethoxysilane, n-hexylmethyldimethoxysilane, n-hexylmethyldiethoxysilane, propylmethyldiethoxysilane, propylmethyldiethoxysilane, propyltriethoxysilane, butyltrimethoxysilane, isobutyltrimethoxysilane, isobutyltriethoxysilane, octyltrimethoxysilane, octyltriethoxysilane, n-octyltrimethoxysilane, n-octyltriethoxysilane, isooctyltrimethoxysilane, isooctyltriethoxysilane, n-hexyltriethoxysilane, cyclohexyltriethoxysilane, n-propyltri-n-butoxysilane, n-propyltrimethoxysilane, n-propyltriethoxysilane, hexadecyltriethoxysilane, hexadecyltrimethoxysilane, octadecyltriethoxysilane, octadecyltrimethoxysilane, octadecylmethyldiethoxysilane, octadecylmethyldimethoxysilane, hexadecylmethyldimethoxysilane and/or hexadecylmethyldiethoxysilane and also mixtures of these silanes, or a mixture comprising at least two of the silanes. Compounds of the formula III may also be selected from ethyltriethoxysilane, ethyltrimethoxysilane, propyltriethoxysilane, propyltrimethoxysilane, butyltriethoxysilane, n-butyltriethoxysilane, n-butyltrimethoxysilane, hexyltriethoxysilane, hexyltrimethoxysilane, n-hexyltriethoxysilane, n-hexyltrimethoxysilane, isohexyltriethoxysilane, isohexyltrimethoxysilane, undecyltriethoxysilane, undecyltrimethoxysilane, decyltriethoxysilane, decyltrimethoxysilane, nonadecyltriethoxysilane, nonadecyltrimethoxysilane, dodecyltriethoxysilane, dodecyltrimethoxysilane, $C_{13}H_{27}$-triethoxysilane, $C_{13}H_{27}$-trimethoxysilane, $C_{14}H_{29}$-triethoxysilane, $C_{14}H_{29}$-trimethoxysilane, $C_{15}H_{31}$-trimethoxysilane, $C_{15}H_{31}$-triethoxysilane, and also the transesterification products thereof.

Particular preference is given to using, in the process, olefinically functionalized alkoxysilane of the general formula II selected from vinyltriethoxysilane and vinyltrimethoxysilane. According to one alternative, olefinically functionalized alkoxysilane of the general formula II is used that is selected from vinyltriethoxysilane, vinyltrimethoxysilane, and alkoxysilanes of the formula III selected from the above.

Particularly preferred combinations of compounds of the formulae II, III and/or IV for preparing the olefinically functionalized siloxane oligomers, and the olefinically functionalized siloxane oligomers obtainable therefrom, are as follows: vinyltriethoxysilane and tetraethoxysilane; vinyltrimethoxysilane and tetramethoxysilane; vinyltriethoxysilane and methyltriethoxysilane; vinyltriethoxysilane, methyltriethoxysilane and tetraethoxysilane; vinyltrimethoxysilane and methyltrimethoxysilane; vinyltrimethoxysilane, methyltrimethoxysilane and tetraethoxysilane or tetramethoxysilane; vinyltriethoxysilane and ethyltriethoxysilane; vinyltriethoxysilane, ethyltriethoxysilane and tetraethoxysilane; vinyltrimethoxysilane and ethyltrimethoxysilane; vinyltrimethoxysilane, ethyltrimethoxysilane and tetraethoxysilane or tetramethoxysilane; vinyltriethoxysilane and propyltriethoxysilane; vinyltriethoxysilane, propyltriethoxysilane and tetraethoxysilane; vinyltrimethoxysilane and propyltrimethoxysilane; vinyltrimethoxysilane, propyltrimethoxysilane and tetraethoxysilane or tetramethoxysilane; vinyltriethoxysilane and isobutyltriethoxysilane; vinyltriethoxysilane, isobutyltriethoxysilane and tetraethoxysilane; vinyltrimethoxysilane and isobutyltrimethoxysilane; vinyltrimethoxysilane, isobutyltrimethoxysilane and tetramethoxysilane; vinyltriethoxysilane and octyltriethoxysilane; vinyltriethoxysilane, octyltriethoxysilane and tetraethoxysilane; in particular with vinyltriethoxysilane and tetraethoxysilane in a ratio of 1:0.20 to 1:0; vinyltrimethoxysilane and octyltrimethoxysilane; vinyltrimethoxysilane, octyltrimethoxysilane and tetramethoxysilane; more particularly with vinyltrimethoxysilane and tetramethoxysilane in a ratio of 1:0.20 to 1:0.

A further aspect of the composition of the invention and of the process of the invention is that the process manages without the use of basic catalysts, especially nitrogen-containing compounds, or of acidic, sulphur-containing ion exchangers. Both catalysts lead to conditions of heterogeneous catalysis. Thus, for example, aqueous ammonia leads to the formation of emulsions, and also the reaction on ion exchangers containing sulphonic acid groups or sulphuric acid groups gives rise to conditions of a heterogeneous catalysis. It has been found that the conditions of a heterogeneous catalysis are not suitable for producing the desired narrow molar mass distribution of siloxane oligomers. Consequently, the compositions of the invention are free from acidic sulphur-containing groups, more particularly sulphuric acid groups or sulphonic acid groups, and/or free from nitrogen-containing compounds, more particularly from nitrogen-containing compounds which are introduced via basic catalysts. In the process of the invention it is also possible to do without the use of metal oxides in combination with an acid; the compositions of the invention are therefore free from metallic residues introduced as a result of adding metal oxides, such as, more particularly, copper oxides, iron oxides, aluminium oxides, copper halides, iron halides, copper hydroxide, iron hydroxide, aluminium hydroxide. Compositions of the invention therefore preferably contain only metals that are intrinsically present, the metal content being preferably less than 0.001 wt % to 0.1 ppm by weight. Correspondingly, in the process of the invention, it is possible to forgo the addition of basic compounds, such as calcium carbonate for the neutralization. The compositions of the invention consequently contain no additionally added calcium, and preferably they contain less than or equal to 1 wt %, more particularly less than or equal to 0.1 wt % to 0.1 ppm by weight, of calcium. The compositions and processes are therefore free from nitrogen-containing compounds, calcium-containing compounds, free from metal-containing compounds, more particularly metal oxides, and free from sulphur-containing compounds, more particularly acidic compounds containing sulphur.

Additionally or alternatively to one of the aforementioned features, it is also possible in the process to use, as processing assistant, at least one silicone oil, such as polydimethylsiloxane, paraffin, liquid paraffin, or a mixture comprising one of these processing assistants. One particularly preferred processing assistant is polydimethylsiloxane, preferably with a kinematic viscosity of approximately 150 to 400 mm$^2$/s; particularly preferred alternatives feature a kinematic viscosity of around 200 mm$^2$/s to around 350 mm$^2$/s.

The invention also provides the following process for preparing the composition, and a composition obtainable by this process, featuring more particularly an especially low chlorine content and preferably a particularly low % content of silicon atoms of monomeric alkoxysilanes, more particularly of below 1.5%, preferably below 1.0% to 0.0%, preferably with the following individual steps:

1) at least one olefinically functionalized alkoxysilane of the formula II, optionally an alkoxysilane of the formula III and/or an alkoxysilane of the formula IV, optionally as a mixture, are preferably introduced as an initial charge; optionally a solvent is added for dilution, such as the corresponding alcohol to the hydrolysis alcohol.
2) At least one acidic hydrolysis and/or condensation catalyst is added, such as HCl, an organic saturated or unsaturated carboxylic acid, in solution in a defined amount of water. The pH set here is preferably less than 7, preferably from 1 to 6, more preferably from 3 to 5. Alternatively it is possible optionally to prepare a mixture (1+2) comprising at least one of the silanes of the formula II, III and/or IV, optionally
    with a defined amount of alcohol, more particularly 0.001 to 5.0 volume units of alcohol per volume unit of alkoxysilane, preferably 0.25 to 1, in relation to the silanes of the formula II, III and/or IV, more particularly methanol or ethanol, depending on alkoxysilane used, and a defined amount of water; preferably the at least one acidic hydrolysis and/or condensation catalyst, such as HCl, an organic saturated or unsaturated carboxylic acid, is in solution in the defined amount of water. The pH set here is preferably less than 7, preferably from 1 to 6, more preferably from 3 to 5. For this purpose, preferably in an initial charge vessel, such as a stirred tank, with mixing, and, as defined amount of water, greater than or equal to 0.5 to 1.5 mol of water, addition takes place. The defined amount of water can be metered continuously or with at least one interruption over a period of 1 to 1000 minutes. The temperature of the reaction mixture is set preferably at 5 to 90° C. for the reaction, preferably at 20 to 55° C., more preferably at 30 to 40° C. or at about 35° C. Following the addition of the mixture, the temperature of the reaction mixture formed is increased further, being set more particularly at the reflux temperature of the alcohol. For example, by heating of the reaction mixture to a temperature of 40 to 80° C., preferably 50 to 80° C., more preferably to around 55 to 80° C., in accordance with the invention to approximately the boiling temperature of the alcohol. The reaction mixture may continue reacting, preferably with mixing, as for example with stirring, over a period of at least 10 minutes to 36 hours, preferably 1 hour (h) to 8 h, at a reaction temperature of 5 to 80° C., preferably 40 to 80° C., and 3) after the end of the reaction, the alcohol is removed. Heating under reflux is carried out preferably for a number of hours, as for example about 2 to 10 hours, preferably 3 to 5 hours, more preferably around 3.5 hours, and subsequently 4) the alcohol, comprising the hydrolysis alcohol and the alcohol introduced, and also, optionally, water, are removed by distillation, preferably under reduced pressure and at elevated temperature, more preferably until the reaction mixture or the resulting composition is substantially solvent-free, more particularly alcohol-free. The alcohol is distilled preferably at a liquid-phase temperature of 0° C. to 90° C. and a pressure of 500 bar to 1 mbar, and at the same time some HCl is distilled off, more preferably at 90° C. to 10° C. and at a pressure of 300 bar to 10 mbar, preferably of 150 mbar to 50 mbar.

5) Subsequently it is possible to set atmospheric pressure; a further defined amount of alcohol is introduced, more particularly 0.001 to 5.0 volume units of alcohol per volume unit of alkoxysilane, and optionally a defined amount of a reducing agent is added, such as alkali metal, preferably sodium, alkaline earth metal, preferably magnesium or calcium, aluminium, metal hydride, preferably Li aluminium hydride, aluminium hydride, or a defined amount of base is added, more particularly gaseous ammonia, Li diisopropylamide, Li isopropylhexylamide, hexamethyldisilazane, alkali metal alkoxide, such as Na or K methoxide or Na or K ethoxide, or alkali metal alkylate, such as butyl-Li, is added. Optionally distillation is carried out again under a pressure of 300 to 10 mbar, and in the case of addition of an alkali metal, the mixture is left to react. The liquid-phase product can be filtered or decanted following the distillation. An alternative or additional possibility is that of contacting with an ion exchanger. The olefinically functionalized siloxane oligomer composition of the invention is obtained with a free alcohol content of less than 2 wt % and a chlorine content of ≤100 mg/kg, based on the composition with a viscosity of less than or equal to 1000 mPa s.

Likewise provided by the invention are compositions obtainable by the process of the invention, comprising olefinically functionalized siloxane oligomers which have not more than one olefinic radical on the silicon atom, and the olefinically functionalized siloxane oligomers comprise Si—O-crosslinked structural elements which form catenary, cyclic, crosslinked and/or three-dimensionally crosslinked structures, the structural elements being derived from alkoxysilanes of the formula II and also, optionally, additionally from alkoxysilanes selected from the formulae III and IV; optionally at least one siloxane oligomer corresponds to the general formula I, with the weight-average molecular weight (Mw) of the siloxane oligomers being greater than or equal to 410 g/mol to 580 g/mol and the number-average molecular weight (Mn) being greater than or equal to 370 to 470 g/mol, and the polydispersity, as the ratio of Mw/Mn, being 1.00 to 1.25, and the structural elements together, in relation to all silicon atoms of the siloxane oligomer, being present at greater than or equal to 3% as T structure.

With particular preference weight-average molecular weights (Mw) of the siloxane oligomers are greater than or equal to 430 g/mol to 550 g/mol and the number-average molecular weight (Mn) is greater than or equal to 400 to 450 g/mol, and the polydispersity, as the ratio of Mw/Mn, is 1.00 to 1.25, 1.00 to 1.20, preferably up to 1.00 to 1.19, and in particular the structural elements together, in relation to all silicon atoms of the siloxane oligomer, are present at greater than or equal to 3% as T structure.

The invention further provides compositions obtainable by the process of the invention, comprising olefinically functionalized siloxane oligomers which have not more than one olefinic radical on the silicon atom, and the olefinically functionalized siloxane oligomers comprise Si—O-crosslinked structural elements which form catenary, cyclic, crosslinked and/or three-dimensionally crosslinked structures, the structural elements being derived from alkoxysilanes of the formula II and also, optionally, additionally from alkoxysilanes selected from the formulae III and IV; preferably at least one siloxane oligomer has a structure of the formula I, there being greater than or equal to 85% (area %, GPC), more particularly greater than or equal to 90%, with a molecular weight Mw of greater than or equal to 250 to less than or equal to 750 g/mol (Mw rel.) present in the overall composition. Alternatively or additionally it is preferred if greater than or equal to 95% have an Mw of greater than or equal to 250 to less than or equal to 1000 g/mol.

In accordance with a further alternative or in addition to aforementioned parameters, preferably, the olefinically functionalized siloxane oligomers are present at greater than or equal to 85% (area %) in relation to the overall composition with a molecular weight of greater than or equal to 250 to 750 g/mol in the overall composition.

With further preference, the olefinically functionalized siloxane oligomers are present in the composition at greater than or equal to 95% (area %), in relation to the overall composition, with a molecular weight of greater than or equal to 250 to 1000 g/mol in the overall composition. The area % figures are always based on the area % of the overall composition. Moreover, the compositions of the invention have a maximum molecular weight of below 2500 g/mol, preferably of below 2200 g/mol, more preferably below 2100 g/mol, i.e. 100% of the composition has a molecular weight of less than or equal to 2100 g/mol.

Likewise preferably in the composition the olefinically functionalized siloxane oligomers are present, at greater than or equal to 75% (area %, GPC), as disiloxane, trisiloxane, tetrasiloxane, pentasiloxane, cyclotrisiloxane, cyclotetrasiloxane, cyclopentasiloxane and/or cyclohexasiloxane, more particularly at greater than or equal to 85%, preferably greater than or equal to 90%, more preferably greater than or equal to 95%.

In the composition it is also possible for the olefinically functionalized siloxane oligomers to be present at greater than or equal to 5% to less than or equal to 50% (area %, GPC) as disiloxane and/or cyclotrisiloxane, more particularly at greater than or equal to 20% to less than or equal to 40%, and greater than or equal to 20% to less than or equal to 50% (area %, GPC) as trisiloxane and/or cyclotetrasiloxane, more particularly at greater than or equal to 20% to less than or equal to 45%, and also greater than or equal to 10% to less than or equal to 30% (area %, GPC) as tetrasiloxane and/or cyclopentasiloxane, more particularly at greater than or equal to 10% to less than or equal to 25%, and greater than or equal to 0% to less than or equal to 20%, preferably less than or equal to 20%, preferably 5% to 20%, 5% to 17%, more preferably 5% to 10%, and
pentasiloxane and/or cyclohexasiloxane are present at greater than or equal to 0% to less than or equal to 20%, more particularly at greater than or equal to 5% to less than 20%, more particularly at greater than or equal to 5% to less than or equal to 10% in the overall composition. In particular, linear or branched hexasiloxanes, cycloheptasiloxanes and siloxane oligomers of higher molecular mass are present at below 10 area % in the overall composition, preferably less than or equal to 9%. The maximum molecular weight here is less than or equal to 2000 g/mol.

With particular preference 70% or more of the siloxane oligomers in the composition are present in the form of disiloxane, cyclotrisiloxane, trisiloxane, cyclotetrasiloxane, tetrasiloxane, cyclopentasiloxane, pentasiloxane and/or cyclohexasiloxane, preferably 75% or more, more preferably 80% or more, with further preference 85% or more. Alternatively with preference greater than or equal to 90% of the siloxane oligomers are present in the form of disiloxanes up to cyclohexasiloxane, but not as linear and/or branched hexasiloxane, cyclohexasiloxane and higher molecular mass.

The invention further provides compositions obtainable by the process of the invention, comprising olefinically functionalized siloxane oligomers which have not more than one olefinic radical on the silicon atom, and the olefinically functionalized siloxane oligomers comprise Si—O-crosslinked structural elements which form catenary, cyclic, crosslinked and/or three-dimensionally crosslinked structures, the structural elements being derived from alkoxysilanes of the formula II and also, optionally, additionally from alkoxysilanes selected from the formulae III and IV; preferably at least one siloxane oligomer has a structure of the formula I, in which the olefinic siloxane oligomers with a molecular weight Mw of greater than or equal to 250 to 500 g/mol are present at greater than or equal to 40%, more particularly at greater than or equal to 45%, preferably between 40% to 70% (area %, GPC), and those with a molecular weight Mw of greater than or equal to 500 to 750 g/mol are present at greater than or equal to 20%, more particularly at greater than or equal to 25%, preferably greater than or equal to 20% to less than or equal to 35%, and those with a molecular weight of greater than or equal to 1000 g/mol are present at less than or equal to 12%, more particularly less than or equal to 10%, very preferably less than or equal to 7% in relation to the overall composition. Molecular weights of 750 to less than or equal to 1000 g/mol may be present, for example in the range up to 15%, more particularly less than or equal to 12% (area %, GPC).

Transesterification products may comprise alkoxysilanes having different alkoxy groups, such as, for example, alkoxysilanes functionalized with methoxy and ethoxy groups, of the formulae II, III, IV or else of the formula I. The siloxane oligomers and the alkoxysilanes of the formulae II, III and IV may be present in the form of transesterification products.

To the skilled person it is clear that the functional siloxane oligomers prepared in this way, depending on their desired application, may be diluted with a diluent or else may be admixed or compounded with a polymer, such as a thermoplastic base polymer, such as PE, PP or an elastomer, such as EVA. Further thermoplastic base polymers and elastomers are given as examples below; the skilled person is aware that in general all thermoplastic base polymers or polymers or elastomers are suitable. The skilled person knows of customary diluents for alkoxysilanes, examples that may be mentioned here being alcohols, ethers, ketones, hydrocarbons, or else mixtures of these. Depending on desired application, therefore, the compositions of the functional alkoxysilanes may be prepared as a concentrate or else as a dilute composition with 99.9 to 0.001 wt %, and also all values situated in between, of functional siloxane oligomers in the overall composition. Preferred dilutions contain 10 to 90 wt % of functional siloxane oligomers, more preferably 20 to 80 wt %, with further preference 30 to 70 wt %.

In order to permit rapid distribution in the extruder, without suffering excessive mass losses in the hot extruders, a balanced ratio between the molecular weight Mw and the TGA temperature at which 5% or 50% mass loss occurs should be maintained. The aforementioned compounds customarily exhibit mass loss of 50% at temperatures above 200° C., more particularly above 220° C. The compositions of the invention are therefore very suitable for use in extruders and at the same time, owing to the very narrow-set molecular weight, permit rapid distribution of the siloxane oligomers in the thermoplastics. Also contributing to this effective distribution are the slightly increased T structures in the siloxanes, since the molecules are more compact.

Thermoplastic base polymers for the purposes of the invention are, in particular, acrylonitrile-butadiene-styrene (ABS), polyamides (PA), polymethyl methacrylate (PMMA), polycarbonate (PC), polyethylene (PE), such as LDPE, LLD-PE, m-PE, polypropylene (PP), polystyrene (PS), polyvinyl chloride (PVC), chloroprene, and also the ethylene-vinyl acetate copolymers (EVA), EPDM or EPM polymers based on ethylene units, and/or celluloid or silane-copolymerized polymers, and, for example, base polymers prepared from unsaturated functional monomers including silanes, such as VTMO, VTEO, and monomers such as ethylene and other olefins, and also monomeric and/or prepolymeric precursor compounds of these base polymers, such as ethylene and propylene. Further preferred elastomers may be selected from the series of ethylene-propylene rubber (EPR), ethylene-propylene-diene rubber (EPDM), styrene-butadiene rubber (SBR), natural rubber (NR), acrylate copolymer rubber (ACM), acrylonitrile-butadiene rubber (NBR) and/or polybutadiene rubber (BR).

The invention also provides for the use of the composition of the invention or of the compositions prepared by the process of the invention as adherence agents, as crosslinking agents by graft polymerization and/or hydrolytic condensation in a conventional way, for producing polymers, prepolymers and/or mineral-filled polymers (compounds) grafted with olefinically functionalized siloxane oligomers, particularly in connection with the production of thermoplastics or elastomers, preferably of mineral-filled thermoplastics, elastomers or prepolymers thereof, for the grafting or in the polymerization of thermoplastic polyolefins, as drying agents, more particularly as water scavengers for silicone sealants, in crosslinkable polymers for producing cables, for preparing crosslinkable polymers, as oil phase in an emulsion and/or together with organosilanes or organopolysiloxanes.

With regard to the joint use, according to the invention, of the composition with organosilanes or organosiloxanes, reference is made in full to the disclosure in EP 1 205 481 B1, more particularly to the disclosure content of paragraph [0039] and to the list of organosilanes and organosiloxanes that is disclosed therein.

Furthermore, compositions of the invention find use advantageous for filler modification (filler coating), resin modification (additive), surface modification (functionalization, hydrophobization), as constituent in coating systems (especially sol-gel systems or hybrid systems), for modifying cathodes and anode materials in batteries, as electrolyte fluid, as additive in electrolyte fluids, for the modification of fibres, more particularly glass fibres and natural fibres, and for modifying textiles, for modifying fillers for the artificial stone industry, as architectural preservative or constituent of architectural preservatives, as addition for mineral-curing compositions, for modifying wood, wood fibres and cellulose. Furthermore, the entire disclosure content of DE 10 2011 086 865.8 with the filing date of 22, Nov. 2011, filed at the German Patent and Trade Mark Office, is made part of the content of the present invention.

The invention is elucidated in more detail by the examples below, without being confined to these working examples.

EXAMPLES

Determination of Molecular Weight:

Molar masses of the molecular weight and also the molar mass distribution can be determined by means of gel permeation chromatography (GPC). The GPC analysis method is described exhaustively in references including "Modern Size-Exclusion Liquid Chromatography", Andre Striegel et al., Wiley & Sons, 2nd edn. 2009. To calibrate the method for siloxane analyses it is possible as standard to use, for example, divinyltetramethoxydisiloxane or divinyltetraethoxydisiloxane. Percentages in relation to the olefinic siloxane oligomers in the present document correspond to a datum in area percent, which can be determined from GPC analyses.

MZ-Analysetechnik columns used: Columns: 50×8.0 mm, MZ-Gel SDplus (styrene/divinylbenzene copolymer with high degree of crosslinking, spherical particle shape), porosity 50 A (angstroms, Å), 5 μm (micrometers) (preliminary column), 300×8.0 mm, MZ-Gel SDplus, porosity 50 A (angstroms, Å), 5 μm, 300×8.0 mm, MZ-Gelplus, porosity 100 A (angstroms, Å), 5 μm, 300×8.0 mm, MZ-Gel SDplus, porosity 500 A (angstroms, Å), 5 μm; eluent and pump flow rate: methyl ethyl ketone (MEK) at 1 ml/min, standard substance: internal standard—1 g/l ethylbenzene in 1% strength sample solution. The instrument is calibrated beforehand against the respective substance (monomer, dimer, trisiloxane, etc.). Instrument from Agilent: 1100 Series isotactic pump G1310A, 1100 Series column oven G1316A, 1100 Series RID detector G1362A, manual injector G1328A, vacuum degasser G1322A, GPC software (PSS WinGPC Unity).

Determination of Chlorine Content and Total Chloride:

The silane is digested with oxygen in a bomb calorimeter and then hydrolysed with acetic acid and hydrofluoric acid. The chloride content of the resulting solution is determined by titration with a well-defined silver nitrate solution.

Determination of Chlorine Content and Hydrolysable Chloride:

After hydrolysis with acetic acid, a determination is made of the chloride content by titration with a well-defined silver nitrate solution.

Determination of SiO2 Content—Crucible Method:

The SiO2 content is determined by acid digestion with concentrated sulphuric acid and subsequent evaporation, by fluorination.

GC Analysis:

As part of the GC standard analysis well known to the skilled person, the monomer content is determined by appropriate calibration and optionally internal standard.

$^{29}$Si NMR Spectrometry:

Furthermore, the monomer content, and also M, D and T structures, can be determined using $^{29}$Si NMR spectrometry, which is likewise well known to the skilled person.

Determination of Dynamic Viscosity:

The dynamic viscosity was determined in accordance with DIN 53015.

1. Syntheses 1.1 VTMO Oligomer with Alcohol Metering—V082

Procedure: A 2 l apparatus is charged with 401.2 g of VTMO (vinyltrimethoxysilane), which is diluted with a fraction of methanol. Subsequently a mixture of methanol, double-distilled water and hydrochloric acid (37%) is metered in at 25° C. under ambient pressure with stirring. There is an exothermic reaction. Should the temperature rise above 45° C., metering is interrupted. The overall reaction time runs to 5 hours, beginning with the metering of the H$_2$O/HCl/methanol mixture. After the reaction, the alcohol is distilled on a rotary evaporator at up to 90° C. and 100 mbar. When the 100 mbar are reached, this pressure is maintained for 15 minutes, after which the apparatus is let down. The liquid phase obtained is a VTMO-siloxane oligomer composition and is identified as "liquid phase 1". At this point, sampling takes place. Liquid phase 1 is mixed further with 256.91 g of methanol and stirred at 25° C. for 30 minutes. The methanol is subsequently distilled on a rotary evaporator at up to 90° C. and 100 mbar. When the 100 mbar are reached, this pressure is maintained for 15 minutes, after which the apparatus is let down. The liquid phase obtained is a VTMO-siloxane oligomer composition based on VTMO, and is called "liquid phase 2".

TABLE 1

| Raw materials V082 | |
|---|---|
| Compound | Initial mass |
| Methanol (dilution) | 83.5 g |
| Methanol (metering) | 173.2 g |
| Hydrochloric acid | 0.43 g |
| Double-distilled water | 39.7 g |

1.2 VTEO-Siloxane Oligomer with Alcohol Metering—V083

Procedure: A 2 l apparatus is charged with 400.0 g of VTEO. Subsequently a mixture of ethanol, double-distilled water and hydrochloric acid (37%) is metered in at 35° C. under ambient pressure with stirring. There is an exothermic reaction. Should the temperature rise above 60° C., metering is interrupted. The total reaction time runs to 5 hours, beginning at 77° C., after complete addition of the H$_2$O/EtOH/HCl mixture. After the reaction, the alcohol is distilled on a rotary evaporator at up to 100° C. and 100 mbar. When the 100 mbar have been reached, they are maintained for 15 minutes, after which the system is let down. The liquid phase obtained is a VTEO-siloxane oligomer composition and is called "liquid phase 1". Sampling takes place. Liquid phase 1 is mixed further with 190.46 g of ethanol and stirred at 35° C. for 30 minutes. Ethanol distillation takes place subsequently on a rotary evaporator at up to 100° C. and 100 mbar. When the 100 mbar are reached, this pressure is maintained for 15 minutes, after which the apparatus is let down. The liquid phase obtained is a VTEO-siloxane oligomer composition and is called "liquid phase 2".

TABLE 2

Raw materials V083

| Compound | Initial mass |
|---|---|
| Ethanol | 190.50 |
| Water | 30.64 |
| Hydrochloric acid | 0.24 |

1.3 VTEO/PTEO-Siloxane Oligomer with Alcohol Metering—V084

Procedure: A 2 l apparatus is charged with 211.7 g of vinyltriethoxysilane (VTEO) and 216.5 g of propyltriethoxysilane (PTEO). Subsequently a mixture of ethanol, double-distilled water and hydrochloric acid (37%) is metered in at 35° C. under ambient pressure with stirring. There is an exothermic reaction. Should the temperature rise above 60° C., metering is interrupted. The total reaction time runs to 5 hours, beginning at 79° C., after complete addition of the $H_2O$/EtOH/HCl mixture. After the reaction, the alcohol is distilled on a rotary evaporator at up to 100° C. and 100 mbar. When the 100 mbar have been reached, they are maintained for 15 minutes, after which the system is let down. The liquid phase obtained is a VTEO/PTEO-siloxane oligomer composition and is referred to as "liquid phase 1". Sampling takes place. Liquid phase 1 is further mixed with 189.50 g of ethanol and stirred at 25° C. for 30 minutes. Ethanol distillation takes place subsequently on a rotary evaporator at up to 100° C. and 100 mbar. When the 100 mbar are reached, this pressure is maintained for 15 minutes, after which the apparatus is let down. The liquid phase obtained is a VTEO/PTEO-siloxane oligomer composition and is called "liquid phase 2".

TABLE 3

Raw materials V084

| Compound | Initial mass |
|---|---|
| Water | 29.6 g |
| Ethanol | 189.5 g |
| HCl | 0.22 g |

2. Ion Exchanger—can be Integrated in the Inventive Process

Example 2.1

150 g of vinyl-/alkyl-functional siloxane co-oligomer (hydrolysable chloride content: 255 wt-ppm or mg/kg) were passed with a flow rate of 2.01 m/h over the ion exchanger Lewatit MP 62 (available from Lanxess) in the OH⁻ form. Working up gave 140.1 g of vinyl-/alkyl-functional siloxane co-oligomer with 32 wt-ppm of hydrolysable chloride. The ethanol content of the odourless product obtained after elution was 18 wt % EtOH. EtOH was removable on a rotary evaporator.

Example 2.2

50 g of vinyl-/alkyl-functional siloxane co-oligomer (hydrolysable chloride content: 110 wt-ppm or mg/kg) were passed with a flow rate of 2.05 m/h over the ion exchanger Lewatit MP 62 (available from Lanxess) in the OH⁻ form. Working up gave 142.8 g of vinyl-/alkyl-functional siloxane co-oligomer with 4 wt-ppm of hydrolysable chloride.

3. Analysis 3.1 General Analysis

TABLE 4

Analytical results from V082, V083 and V084

| Experiment No. | V082 | | V083 | | V084 | |
|---|---|---|---|---|---|---|
| | "Liquid phase 1" | "Liquid phase 2" | "Liquid phase 1" | "Liquid phase 2" | "Liquid phase 1" | "Liquid phase 2" |
| Total chloride [mg/kg] | <35 | 40 | 35 | <35 | 115 | 70 |
| Hydrol. chloride [mg/kg] | 24 | 4 | 3 | <3 | 4 | 4 |
| $SiO_2$ [Mass %] | 54.7 | 54.9 | 45.4 | 45.4 | 41.6 | 41.6 |
| Free alcohol [mass %] | 0.3 | 0.2 | 0.7 | 0.7 | 0.5 | 0.5 |
| Monomer [mass %] | 1.7 | 0.7 | 1.5 | 0.9 | 3.2 | 2.5 |

3.2. GPC Analyses

TABLE 5a

Results of the GPC analyses for Examples V082, V083 and V084

| Experiment No. | Mn [g/mol] | Mw [g/mol] | D |
|---|---|---|---|
| V082 liquid phase 1 | 424.50 | 516.97 | 1.2191 |
| V082 liquid phase 2 | 425.90 | 513.49 | 1.2056 |
| V083 liquid phase 1 | 409.36 | 476.39 | 1.1638 |
| V083 liquid phase 2 | 426.97 | 492.92 | 1.1545 |
| V084 liquid phase 1 | 416.27 | 456.23 | 1.0960 |
| V084 liquid phase 2 | 423.00 | 464.28 | 1.0976 |

TABLE 5b

Results of the GPC analyses for further siloxane oligomers prepared in analogy to Examples 1.1-V082, Ex. 1.2-V083 and Ex. 1.3-V084.

| analogous experiments | Mn g/mol | Mw g/mol | D | Mmax [g/mol] |
|---|---|---|---|---|
| V082 liquid phase 1 | 474 | 556.3 | 1.17 | 2000 |
| V082 liquid phase 2 | 482.9 | 561.1 | 1.16 | 2000 |
| V083 liquid phase 1 | 435.4 | 488.2 | 1.12 | 1300 |
| V083 liquid phase 2 | 447.9 | 503.4 | 1.12 | 1500 |
| V084 liquid phase 1 | 427.2 | 469.7 | 1.09 | 1200 |
| V084 liquid phase 2 | 427.7 | 475.7 | 1.11 | 1200 |

TABLE 5c

| Analogous to | <Disiloxane [%] | Disiloxane + cyclotrisiloxane [%] | Trisiloxane + cyclotetrasiloxane [%] | Tetrasiloxane + cyclopentasiloxane [%] | Pentasiloxane + cyclohexasiloxane [%] | >Pentasiloxane [%] |
|---|---|---|---|---|---|---|
| V082 liquid phase 1 | <0.1 | 8.9 | 25.8 | 23.3 | 14.8 | 17.3 |
| V082 liquid phase 2 | <0.1 | 8.5 | 25.5 | 23.4 | 15.2 | 27.5 |
| V083 liquid phase 1 | 1.4 | 25.1 | 39.8 | 17.7 | 8.4 | 7.6 |
| V083 liquid phase 2 | <0.1 | 23.4 | 40.5 | 18.2 | 8.9 | 8.9 |
| V084 liquid phase 1 | 2.5 | 36.5 | 38 | 14.1 | 5.5 | 3.5 |
| V084 liquid phase 2 | 2 | 35.2 | 38 | 14.5 | 5.9 | 4.4 |

For key see Table 5d

TABLE 5d

Results of the GPC analyses (fractions in area %) of the further siloxane oligomers prepared in analogy to Examples 1.1-V082, Ex. 1.2-V083 and Ex. 1.3-V084.

| | 0-250 rel. MW [%] | 250-500 rel. MW [%] | 500-750 rel. MW [%] | 750-1000 rel. MW [%] | >1000 rel. MW [%] |
|---|---|---|---|---|---|
| V082 liquid phase 1 | 1.46 | 48.84 | 32.03 | 12.21 | 5.47 |
| V082 liquid phase 2 | 1.35 | 48.12 | 32.47 | 12.45 | 5.61 |
| V083 liquid phase 1 | 1.85 | 63.56 | 26.44 | 6.65 | 1.5 |
| V083 liquid phase 2 | 0.51 | 62.57 | 27.41 | 7.41 | 2.1 |
| V084 liquid phase 1 | 2.45 | 66.73 | 25.47 | 4.64 | 0.71 |
| V084 liquid phase 2 | 2 | 65.81 | 25.96 | 5.26 | 0.97 |

TABLE 6

Results from NMR analyses for V082

| | | Fractions in the siloxane oligomer compositions | | | |
|---|---|---|---|---|---|
| Experiment No. | $^1$H and $^{13}$C NMR | Silane monomer [mol %] | M structure [mol %] | D structure [mol %] | T structure [mol %] |
| V082 liquid phase 1 | 1.4 mol SiOMe | 1.1 (VTMO) | 41.1 | 49.8 | 8.0 |
| V082 liquid phase 2 | 1.3 mol SiOMe | 0.5 (VTMO) | 40.4 | 50.4 | 8.7 |

TABLE 7

Results from NMR analyses for V083

| | | Fractions in the siloxane oligomer compositions | | | |
|---|---|---|---|---|---|
| Experiment No. | $^1$H and $^{13}$C NMR | Silane monomer [mol %] | M structure [mol %] | D structure [mol %] | T structure [mol %] |
| V083 liquid phase 1 | 1.4 mol SiOEt | 1.0 (VTEO) | 56.2 | 39.8 | 3.0 |
| V083 liquid phase 2 | 1.4 mol SiOEt | 0.6 (VTEO) | 52.7 | 42.6 | 4.1 |

TABLE 8

Results from NMR analyses for V084

| | | Fractions in the siloxane oligomer compositions | | | |
|---|---|---|---|---|---|
| Experiment No. | $^1$H and $^{13}$C NMR | Silane monomer [mol %] | M structure [mol %] | D structure [mol %] | T structure [mol %] |
| V084 Liquid phase 1 | 3.0 mol SiOEt and 0.94 mol propylsilyl | — (VTEO) 1.8 (PTEO) | 33.4 33.9 | 17.6 12.4 | 0.9 — |
| V084 Liquid phase 2 | 3.0 mol SiOEt and 0.94 mol propylsilyl | — (VTEO) 1.4 (PTEO) | 33.8 35.1 | 16.4 12.3 | 1.0 — |

4. Comparative Examples

Comparative Example 1

V078—Example 1 from EP0518057 B1—Preparation of a co-condensate of vinyltrimethoxysilane and methyltrimethoxysilane with a molar vinyl:methoxy groups ratio of around 1:3.

Procedure: A 2 l four-necked apparatus with water-operated condenser and magnetic stirrer was charged with 397.6 g of vinyltrimethoxysilane (VTMO) and 244.6 g of methyltrimethoxysilane at 20° C. The mixture was admixed, using a 500 ml dropping funnel, with a solution of 49.9 g of distilled water in 332.8 g of methanol, this solution containing 2400 ppm of hydrogen chloride. After a total of 16 hours, the entire methanol together with HCl was distilled off at about 300 mbar. Thereafter the resulting oligomer mixture was distilled to a pressure of about 1 mbar and a boiling range ending at 113° C. In this way, 170 g of clear product were obtained.

TABLE 9

Raw materials V078

| Compound | Supplier | Initial mass |
| --- | --- | --- |
| VTMO | Evonik Degussa GmbH | 397.6 g |
| MTMS | Evonik Degussa GmbH | 244.6 g |
| Hydrochloric acid 2400 ppm | Merck (HCl 37%) Double-distilled water | 49.9 g |
| Methanol | ROTH | 332.8 g |

Comparative Example 2

V081—Example 6 from EP 0518057 B1—Preparation of a condensate of vinyltrimethoxysilane with a molar vinyl:methoxy groups ratio of about 1:1.75. Procedure: A 2 l four-necked apparatus with water-operated condenser and magnetic stirrer was charged with 693.83 g of VTMO at 20° C. The mixture was admixed with a solution of 52.82 g of distilled water in 351.53 g of methanol, the solution containing 1100 ppm of hydrogen chloride. A 500 ml dropping funnel was used for this purpose. The temperature rose to about 36° C. within 26 minutes. After a total of 13 hours, the entire methanol together with hydrochloric acid was removed by distillation under about 300 mbar within 2-3 hours. The resulting oligomer mixture was thereafter distilled down to a pressure of about 1 mbar and a boiling range ending at 100° C. In this way, 240 g of clear product were obtained.

TABLE 10

Raw materials V081

| Compound | Supplier | Initial mass |
| --- | --- | --- |
| VTMO | Evonik Degussa GmbH | 693.7 g |
| Methanol | | 351.5 g |
| Hydrochloric acid 1100 ppm | Merck (HCl 37%) Double-distilled water | 52.8 g |

Analytical Results for the Comparative Experiments:

TABLE 11

Analytical results for V078 (Comparative Example 1)

| Experiment No. V078 | Total chlorides [mg/kg] | hydrolysable chloride [mg/kg] | $SiO_2$ (mass) [%] | VTMO (mass) [%] | Colour number [mg Pt—Co/l] |
| --- | --- | --- | --- | --- | --- |
| Distillate (cf. Example 1 in EP0518057B1) | 230 | 16 | 52.4 | <0.1 | <5 |

TABLE 12

Analytical results for V081 (Comparative Example 2)

| Experiment No. V081 | Total chloride [mg/kg] | hydrolysable chloride [mg/kg] | $SiO_2$ (mass) [%] | VTMO (mass) [%] | Colour number [mg Pt—Co/l] |
| --- | --- | --- | --- | --- | --- |
| Distillate (cf. Example 6 in EP0518057B1) | 50 | <3 | 48.6 | 1.7 | <5 |

TABLE 13

Evaluation of the GPC analysis results

| Experiment number | Mn [g/mol] | Mw [g/mol] | D = Mw/Mn |
| --- | --- | --- | --- |
| V078 | 275.13 | 291.11 | 1.0581 |
| V081 | 254.06 | 269.90 | 1.0624 |

TABLE 14

Results from the $^{29}Si$ NMR analyses on the products from Comparative Experiments V078 and V081, [VS = vinylsilyl, MS = methylsilyl]

| Comparative Experiment No. | Fractions in the siloxane oligomer compositions | | | |
| --- | --- | --- | --- | --- |
| | M structure [mol %] | D structure [mol %] | T structure [mol %] | Silane monomer [mol %] |
| V078 | 52.1 (VS) | 9.1 (VS) | —(VS) | 0.9 (VTMO) |
| | 29.3 (MS) | 8.6 (MS) | —(MS) | — (MTMS) |
| V081 | 91.8 (VS) | 6.8 (VS) | —(VS) | 1.2 (VTMO) |

5. Performance Experiments

TABLE 14

Product assignment for performance experiments

| Product from experiment No. | Performance experiment No. |
| --- | --- |
| V082 liquid phase 1 | — |
| V082 liquid phase 2 | V127 |
| V083 liquid phase 1 | — |
| V083 liquid phase 2 | V128 |
| V084 liquid phase 1 | — |
| V084 liquid phase 2 | V129 |
| V078 | V116 |
| V081 | V118 |

5.1 Kneading Experiments

The following kneading operations were operated with a temperature profile of "3 min at 140° C., from 140° C. to 170° C. in 2 min, 5 min at 170° C." with a rotary speed of 30 rpm in a HAAKE kneading apparatus. Subsequently, each batch was processed by compression to form two plates at 190° C. under a load pressure of 20 t. In order to simplify the addition of the peroxide, silane/peroxide solutions were prepared.

5.2 Preparation of the Measurement Specimens

The samples prepared were stored in a conditioning chamber at 23° C. and 50% relative humidity, after which specimens were made for tensile tests and for the determination of the water uptake capacity and determination of the melt index.

TABLE 15

Raw materials and batches for practical application

| Compound | Batch |
|---|---|
| ATH | M56/15 |
| EVA | M56/156 |
| DCUP | M56/026 |

TABLE 16

Peroxide mixtures for kneadings

| Siloxane oligomer/DCUP solution batch | Initial mass DCUP | Initial siloxane oligomer mass | for performance experiment No. |
|---|---|---|---|
| V078 | 9.81 g | 0.19 g | V116 |
| V081 | 9.81 g | 0.19 g | V118 |
| V082 | 9.81 g | 0.19 g | V127 |
| V083 | 9.81 g | 0.19 g | V128 |
| V084 | 9.82 g | 0.19 g | V129 |

TABLE 17

Initial masses in the kneading experiments

| Experiment No. | Initial mass EVA | Initial mass ATH | Initial DCUP/silanoxane oligomer solution | Silane oligomer/DCUP solution batch |
|---|---|---|---|---|
| V116 | 27.72 g | 41.61 g | 0.45 g | V078 |
| V118 | 27.72 g | 41.61 g | 0.44 g | V081 |
| V127 | 27.72 g | 41.61 g | 0.42 g | V082 |
| V128 | 27.72 g | 41.61 g | 0.42 g | V083 |
| V129 | 27.72 g | 41.61 g | 0.44 g | V084 |
| V153 (blank sample) | 27.72 g | 41.61 g | — | — |

5.3 Determinations of the Melt Index (MFR) and the Volume Flow Index (MVR)

Preparation and evaluation took place in accordance with DIN ISO 1133 (Method B), the content of which is referenced in full and made part of the content of the present application. Testing apparatus: Zwick 4106 flow tester. The determination of melt index (MFR) and volume flow index (MVR) is carried out under a fixed shearing load and at defined temperature ($T_{PT}$) and defined loading ($m_{nom}$) on a polymeric melt through a standard nozzle. The change in travel of the die over time is ascertained, and MVR and MFR are calculated according to the formulae known to the skilled person. ~7 g of the individual samples were comminuted and the melt index ("MFR") was determined at a temperature of 160° C. under a load of 21.6 kg.

TABLE 18

Results for the analysis of the melt index (MFR) and volume flow index (MVR) from V116 and V118

| | Experiment No. | |
|---|---|---|
| | V116 | V118 |
| Siloxane oligomer from | V078 | V081 |
| Experimental temperature | 160° C. | |
| Preheating time | 4 min | |
| Loading weight | 21.6 kg | |
| MFR [g min] | 3.19 | 3.39 |
| MVR [cm³ min] | 2.36 | 2.51 |
| Density [g/cm³] | 1.352 | 1.348 |

TABLE 19

Results for the analysis of the melt index (MFR) and volume flow index (MVR) from V127, V128, V129 and V153 (blank sample)

| | Experiment No. | | | |
|---|---|---|---|---|
| | V153 | V127 | V128 | V129 |
| Siloxane oligomer from | — | V082 | V083 | V084 |
| Experimental temperature | 160° C. | | | |
| Preheating time | 4 min | | | |
| Loading weight | 21.6 kg | | | |
| MFR [g min] | 2.03 | 3.27 | 3.47 | 3.67 |
| MVR [cm³ min] | 1.50 | 2.43 | 2.57 | 2.72 |
| Density [g/cm³] | 1.349 | 1.350 | 1.351 | 1.351 |

5.4 Water Uptake Capacity

5.4.1 Determination of Water Uptake Capacity

Test specimens of defined geometry are stored under defined conditions (temperature, time) in a water bath. The change in weight of the samples is captured before and during storage and after the drying operations.

The water uptake capacity was determined using the specimens produced, after a time period of 24 hours, by means of a triple determination, with the specimens having been stored in the water bath at 70° C. for the stated period.

TABLE 20

Results of water uptake capacity

| Experiment No. | Value [mg/cm] after 7 d storage |
|---|---|
| V153 | 3.81 |
| V116 | 1.55 |
| V118 | 1.40 |
| V127 | 1.22 |
| V128 | 1.64 |
| V129 | 1.64 |

5.5 Determination of Tensile Properties

The tensile properties were determined in accordance with DIN EN ISO 527-1, 527-2, 527-3, the content of which is referenced in full and made part of the content of the present application. For this purpose, a sample rod of defined geometry is clamped into the tensile testing machine and subjected to uniaxial loading until breakage occurs (uniaxial extension at defined extension rate). The change in stress is recorded on the sample rod via the extension of the specimen, and the tensile strength and elongation at break are ascertained. Testing instrument: Zwick 4115 universal tester. Using the specimens or tensile rods ("bones") produced, after 24 h of storage in a conditioning chamber at 23°

C. and 50% relative humidity, the tensile properties (elongation at break and tensile strength) of the samples were determined in a five-fold determination, using a testing speed of 200 mm/min and a pre-tensioning force of 0.2 MPa.

TABLE 21

Complete overview of results for tensile properties and elongations at break

| Product from experiment No. | PF experiment No. | Elongation at break [%] | Tensile strength [MPa] |
|---|---|---|---|
| V082 | V127 | 73.81 | 8.87 |
| V083 | V128 | 88.01 | 8.14 |
| V084 | V129 | 55.15 | 8.07 |
| V078 | V116 | 80.37 | 8.66 |
| V081 | V118 | 85.61 | 9.31 |

The invention claimed is:

1. A process for preparing a composition comprising olefinically functionalized siloxane oligomers, the process comprising reacting:
(i) an olefinically functionalized alkoxysilane of formula II, $$A\text{-Si}(R^2)_x(OR^1)_{3-x} \tag{II}$$

wherein A in formula II represents an olefinic radical and is a linear, branched or cyclic alkenyl- or cycloalkenyl-alkylene-functional group having in each case 2 to 16 C atoms;
$R^2$ represents a linear, branched or cyclic alkyl radical having 1 to 15 C atoms and x is 0 or 1; and
each $R^1$, independently, represents a linear, branched or cyclic alkyl radical having 1 to 4 C atoms,
(ii) in the presence of at least one of a hydrolysis and a condensation catalyst that comprises hydrogen chloride;
(iii) and in the presence of water and alcohol as solvent, to produce the olefinically functionalized siloxane oligomers; and
(iv) removing the hydrolysis alcohol and the solvent present; and
(v) at least once during said (iv) removing or subsequently, further adding alcohol and carrying out removal;
(vi) wherein the total chloride content of the composition is less than or equal to 100 mg/kg; and
(vii) the weight-average molecular weight (Mw) is 410 g/mol to 580 g/mol,
wherein
a) in (iii) the reaction takes place in the presence of water and an alcohol in an amount of 0.001 to 5.0 volume units of alcohol per volume unit of alkoxysilane, and/or
b) in (v), at least once during step (iv) or subsequently, additional alcohol is added and removal is carried out 1 to 6 times.

2. The process of claim 1, further comprising reacting the olefinically functionalized alkoxysilane of formula II the presence of at least one of a hydrolysis and a condensation catalyst with
(i.1) at least one alkoxysilane of formula III, $$B\text{—Si}(R^4)_y(OR^3)_{3-y} \tag{III},$$

wherein B represents a saturated hydrocarbon radical and is a linear, branched or cyclic alkyl radical having 1 to 16 C atoms;

each $R^3$, independently, represents a linear, branched or cyclic alkyl radical having 1 to 4 C atoms;
$R^4$ represents a linear, branched or cyclic alkyl radical having 1 to 15 C atoms; and
y is 0 or 1.

3. The process of claim 1, further comprising reacting the olefinically functionalized alkoxysilane of general formula II in the presence of at least one of a hydrolysis and a condensation catalyst with
(i.2) at least one tetraalkoxysilane of formula IV, $$\text{Si}(OR^3)_4 \tag{IV},$$

wherein:
each $R^3$, independently, represents a linear, branched or cyclic alkyl radical having 1 to 4 C atoms.

4. The process of claim 1, wherein
the alcohol is methanol, ethanol or any combination thereof.

5. The process of claim 1, wherein
the composition is obtained following (v) as a liquid-phase product.

6. The process of claim 2, wherein:
in the olefinically functionalized alkoxysilane of general formula II:

$$A\text{-Si}(R^2)_x(OR^1)_{3-x} \tag{II}$$

A is selected from the group consisting of vinyl, allyl, butenyl, pentenyl, hexenyl, ethylhexenyl, heptenyl, octenyl, cyclohexenyl-C1 to C8-alkylene, and a 3'-cyclohexenyl-2-ethylene group;
x is 0 or 1; and
$R^1$ are each independently a methyl, ethyl or propyl group; and
in the alkoxysilane of formula III:

$$B\text{—Si}(R^4)_y(OR^3)_{3-y} \tag{III}$$

the unsubstituted hydrocarbon radical B is selected from the group consisting of methyl, ethyl, propyl, butyl, isobutyl, n-butyl, tert-butyl, pentyl, n-pentyl, isopentyl, neopentyl, hexyl, isohexyl, neohexyl, 2,2-dimethylbutyl, 2,3-dimethylbutyl, 2-methylpentyl, 3-methylpentyl, octyl, n-octyl, isooctyl, nonyl, decyl, undecyl, dodecyl, $C_{13}H_{27}$, $C_{14}H_{29}$, $C_{15}H_{31}$ and a hexadecyl group; and
$R^3$ is a methyl, ethyl or propyl group; and
y is 0 or 1.

7. The process of claim 2, wherein
in the olefinically functionalized alkoxysilane of the general formula II
x is 0 and/or in the alkoxysilane of the formula III functionalized with a saturated hydrocarbon radical y is 0.

8. The process of claim 2, wherein
water is added of greater than or equal to 0.60 to 1.48 mol of water per mole of silicon atoms in the alkoxysilanes of at least one of formula II and formula III.

9. The process of claim 2, further comprising
at least partial hydrolysis and condensation of the alkoxysilane of at least one of formula II and formula III in the presence of an acidic catalyst; and, optionally removing the alcohol.

10. The process of claim 9, wherein
the acidic catalyst is hydrogen chloride.

11. The process of claim 1, wherein
in (iii) the reaction takes place in the presence of water and an alcohol in an amount of 0.0.5 to 2.5 volume units of alcohol per volume unit of alkoxysilane.

12. The process of claim 2, wherein the olefinically functionalized alkoxysilane of formula II is selected from the group consisting of vinyltriethoxysilane, allyltriethoxysilane, butenyltriethoxysilane, pentenyltriethoxysilane, hexenyltriethoxysilane, ethylhexenyltriethoxysilane, heptenyltriethoxysilane, octenyltriethoxysilane, cyclohexenyl-C1 to C8-alkylenetriethoxysilane, cyclohexenyl-2-ethylenetriethoxysilane, 3'-cyclohexenyl-2-ethylenetriethoxysilane, cyclohexadienyl-C1 to C8-alkylenetriethoxysilane, cyclohexadienyl-2-ethylenetriethoxysilane, vinyltrimethoxysilane, allyltrimethoxysilane, butenyltrimethoxysilane, pentenyltrimethoxysilane, hexenyltrimethoxysilane, ethylhexenyltrimethoxysilane, heptenyltrimethoxysilane, octenyltrimethoxysilane, cyclohexenyl-C1 to C8-alkylenetrimethoxy silane, cyclohexenyl-2-ethylenetrimethoxysilane, 3'-cyclohexenyl-2-ethylenetrimethoxysilane, cyclohexadienyl-C1 to C8-alkylenetrimethoxysilane and cyclohexadienyl-2-ethylenetrimethoxysilane; and in each case independently the alkoxysilane of formula III is selected from the group consisting of methyltriethoxysilane, ethyltriethoxysilane, n-propyltriethoxysilane, isopropyltriethoxysilane, butyltriethoxysilane, n-butyltriethoxysilane, isobutyltriethoxysilane, hexyltriethoxysilane, n-hexyltriethoxysilane, isohexyltriethoxysilane, heptyltriethoxysilane, octyltriethoxysilane, n-octyltriethoxysilane, isooctyltriethoxysilane, undecyltriethoxysilane, decyltriethoxysilane, nonadecyltriethoxysilane, dodecyltriethoxysilane, $C_{13}H_{27}$-triethoxysilane, $C_{14}H_{29}$-triethoxysilane or $C_{15}H_{31}$-triethoxysilane, hexadecyltriethoxysilane, methyltrimethoxysilane, ethyltrimethoxysilane, n-propyltrimethoxysilane, isopropyltrimethoxysilane, butyltrimethoxysilane, n-butyltrimethoxysilane, isobutyltrimethoxysilane, hexyltrimethoxysilane, n-hexyltrimethoxysilane, isohexyltrimethoxysilane, heptyltrimethoxysilane, octyltrimethoxysilane, n-octyltrimethoxysilane, isooctyltrimethoxysilane, undecyltrimethoxysilane, decyltrimethoxysilane, nonadecyltrimethoxysilane, dodecyltrimethoxysilane, $C_{13}H_{27}$-trimethoxysilane, $C_{14}H_{29}$-trimethoxysilane or $C_{15}H_{31}$-trimethoxysilane and hexadecyltrimethoxysilane.

13. The process of claim 1, wherein
the hydrolysis alcohol and the solvent are removed by distillation.

14. The process of claim 3, further comprising
at least partial hydrolysis and condensation of the alkoxysilane of at least one of formula II and formula IV in the presence of an acidic catalyst; and, optionally
removing the alcohol.

15. The process of claim 12, wherein
in (iii) the reaction takes place in the presence of water and an alcohol in an amount of 0.1 to 2.0 volume units of alcohol per volume unit of alkoxysilane.

16. The process of claim 1, further comprising reacting the olefinically functionalized alkoxysilane of formula II the presence of at least one of a hydrolysis and a condensation catalyst with at least one of:

(i.1) at least one alkoxysilane of formula III, $$B—Si(R^4)_y(OR^3)_{3-y} \quad (III),$$

wherein B represents a saturated hydrocarbon radical and is a linear, branched or cyclic alkyl radical having 1 to 16 C atoms;

each $R^3$, independently, represents a linear, branched or cyclic alkyl radical having 1 to 4 C atoms;

$R^4$ represents a linear, branched or cyclic alkyl radical having 1 to 15 C atoms; and y is 0 or 1; and (i.2) at least one tetraalkoxysilane of formula IV, $$Si(OR^3)_4 \quad (IV),$$

wherein:

each $R^3$, independently, represents a linear, branched or cyclic alkyl radical having 1 to 4 C atoms.

17. The process of claim 16, wherein
greater than or equal to 1% of the silicon atoms in the olefinically functionalized siloxane oligomer, in relation to the sum total of silicon atoms in the siloxane oligomer, are obtained as a T structure, and/or
the amount of silicon atoms in monomeric alkoxysilanes represented by at least one of formula II, formula III and formula IV, or the hydrolysis product thereof, is less than or equal to 3% in relation to the total silicon atoms in the composition.

18. The process of claim 1, wherein the hydrolysis catalyst or the condensation catalyst comprises hydrogen chloride.

* * * * *